United States Patent

Karanewsky et al.

Patent Number: 4,745,196
Date of Patent: May 17, 1988

[54] ORALLY ACTIVE PHOSPHONYL HYDROXYACYL PROLINES

[75] Inventors: Donald S. Karanewsky, East Windsor; Edward W. Petrillo, Jr., Pennington, both of N.J.

[73] Assignee: E. R. Squibb & Sons, Inc., Princeton, N.J.

[21] Appl. No.: 816,476

[22] Filed: Jan. 6, 1986

[51] Int. Cl.$^4$ .................. C07F 9/65; A61K 31/675
[52] U.S. Cl. .................. 548/413; 546/22; 548/414
[58] Field of Search .......... 546/413; 514/91

[56] References Cited

U.S. PATENT DOCUMENTS 4,452,790  6/1984  Karanewsky et al. ......... 548/414 X
4,452,791  6/1984  Ryono et al. .............. 548/413 X

FOREIGN PATENT DOCUMENTS 0097534  1/1984  European Pat. Off. ......... 548/413

OTHER PUBLICATIONS

Rubin et al., SQ14,225 (D-3-Mercapto-2-Methyl-propanoyl-L-Proline), . . . Jour. of Pharm. & Exp. Therapeutics, vol. 204, pp. 271-280.

Primary Examiner—Donald G. Daus
Assistant Examiner—Diana G. Rivers
Attorney, Agent, or Firm—Lawrence S. Levinson; Stephen B. Davis

[57] ABSTRACT

This invention is directed to orally active antihypertensive agents of the formula

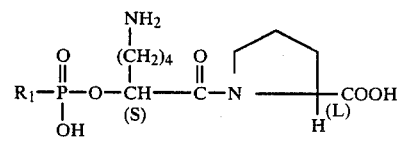

wherein $R_1$ is certain alkyl or aralkyl groups.

3 Claims, No Drawings

ORALLY ACTIVE PHOSPHONYL HYDROXYACYL PROLINES

BACKGROUND OF THE INVENTION

Karanewsky et al. disclose antihypertensive phosphonyl hydroxyacyl amino acids of the formula $$R_1-\overset{\overset{O}{\|}}{\underset{\underset{OR_3}{|}}{P}}-O-CH-\overset{\overset{R_2}{|}}{\underset{}{}}-\overset{\overset{O}{\|}}{C}-X$$

wherein X includes L-proline in U.S. Pat. No. 4,452,790.

SUMMARY OF THE INVENTION

This invention is directed to processes for preparing phosphonyl hydroxyacyl proline compounds. These processes involve a phosphonous acid intermediate of a phosphonochloridate intermediate. The resulting final products possess angiotensin converting enzyme inhibition activity and are useful as antihypertensive agents.

This invention is also directed to certain phosphonyl hydroxyacyl proline compounds of the formula $$R_1-\overset{O}{\underset{OH}{\overset{\|}{P}}}-O-\underset{(S)}{CH}-\overset{NH_2}{\underset{}{\overset{(CH_2)_4}{|}}}-\overset{O}{\underset{}{\overset{\|}{C}}}-N\underset{H\ (L)}{\underbrace{\qquad}}-COOH \quad (I)$$

and pharmaceutically acceptable salts thereof wherein $R_1$ is

⟨phenyl⟩-(CH$_2$)$_2$—,  ⟨phenyl⟩-(CH$_2$)$_3$—,

⟨phenyl⟩-(CH$_2$)$_4$—,  F-⟨phenyl⟩-(CH$_2$)$_4$—,

⟨phenyl⟩-(CH$_2$)$_5$—,  H$_3$C—(CH$_2$)$_4$—,  H$_3$C—(CH$_2$)$_5$—,

H$_3$C—(CH$_2$)$_6$—, or H$_3$C—(CH$_2$)$_7$—.

These compounds of formula I are especially useful as antihypertensive agents due to their outstanding oral activity.

The most preferred compound of formula I is the compound wherein $R_1$ is

⟨phenyl⟩-(CH$_2$)$_4$—.

DETAILED DESCRIPTION OF THE INVENTION

According to one process of this invention, a phosphonous acid of the formula $$R_2-\overset{O}{\underset{H}{\overset{\|}{P}}}-OH \quad (II)$$

is coupled to the hydroxyacyl proline ester of the formula $$HO-\overset{R_3}{\underset{}{\overset{|}{CH}}}-\overset{O}{\underset{}{\overset{\|}{C}}}-N\underset{H\ (L)}{\underbrace{\qquad}}-COOR_4 \quad (III)$$

wherein $R_4$ is an easily removable ester protecting group such as benzyl or methyl in the presence of dicyclohexylcarbodiimide and N,N-dimethylaminopyridine. This reaction is performed in a solvent such as tetrahydrofuran and yields the intermediate of the formula $$R_2-\overset{O}{\underset{H}{\overset{\|}{P}}}-O-\overset{R_3}{\underset{}{\overset{|}{CH}}}-\overset{O}{\underset{}{\overset{\|}{C}}}-N\underset{H}{\underbrace{\qquad}}-COOR_4. \quad (IV)$$

The intermediate of formula IV is oxidized with an oxidizing agent such as sodium periodate to give the ester product of the formula $$R_2-\overset{O}{\underset{OH}{\overset{\|}{P}}}-O-\overset{R_3}{\underset{}{\overset{|}{CH}}}-\overset{O}{\underset{}{\overset{\|}{C}}}-N\underset{H\ (L)}{\underbrace{\qquad}}-COOR_4. \quad (V)$$

Removal of the $R_4$ ester group, for example, by hydrogenation when $R_4$ is benzyl or treatment with lithium hydroxide when $R_4$ is methyl yields the phosphonyl hydroxyacyl proline final products of the formula $$R_2-\overset{O}{\underset{OH}{\overset{\|}{P}}}-O-\overset{R_3}{\underset{}{\overset{|}{CH}}}-\overset{O}{\underset{}{\overset{\|}{C}}}-N\underset{H\ (L)}{\underbrace{\qquad}}-COOH. \quad (VI)$$

Alternatively, the phosphonous acid of formula II can be reacted with the alcohol of the formula $$HO-\overset{R_3}{\underset{}{\overset{|}{CH}}}-COOCH_3 \quad (VII)$$

in the presence of dicyclohexylcarbodiimide and N,N-dimethylaminopyridine to give the intermediate of the formula

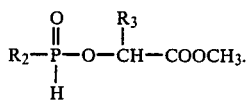  (VIII)

This intermediate is then oxidized as described above to give

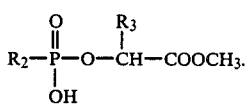  (IX)

Removal of the methyl ester group such as by treatment with lithium hydroxide gives the corresponding carboxylic acid which is then coupled with the proline ester of the formula

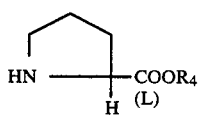  (X)

in the presence of dicyclohexylcarbodiimide or carbonyl diimidazole to give the ester of formula V.

According to another process of this invention a phosphonic diester of the formula

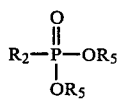  (XI)

wherein $R_5$ is an easily removable ester group such as benzyl or methyl is treated with phosphorus pentachloride to give the phosphonochloridate of the formula

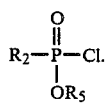  (XII)

The phosphonochloridate of formula XII is treated with the hydroxyacyl proline ester of formula III in the presence of N,N-dimethylaminopyridine and triethylamine to yield the diester of the formula

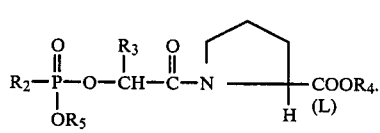  (XIII)

Removal of the $R_4$ and $R_5$ ester protecting groups such as by hydrogenation when $R_4$ and $R_5$ are both benzyl yields the phosphonyl hydroxyacyl proline final products of formula VI.

Alternatively, the phosphonochloridate of formula XII wherein $R_5$ is benzyl can be reacted with the alcohol of formula VII in the presence of dicyclohexylcarbodiimide and N,N-dimethylaminopyridine to give the intermediate of the formula

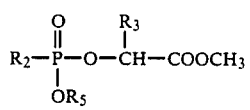  (XIV)

Removal of the methyl ester group gives the corresponding carboxylic acid which can then be coupled in the presence of dicyclohexylcarbodiimide or carbonyl diimidazole to the proline ester of formula X to give the diester intermediate of formula XIII.

In the above reactions the variables have the meanings set forth below:

$R_2$ is straight or branched chain alkyl of 1 to 10 carbons, —(CH$_2$)$_s$—NH$_2$, —(CH$_2$)$_s$—halo wherein halo is Cl, Br, or F, —(CH$_2$)$_q$—cycloalkyl wherein cycloalkyl is a saturated ring of 4 to 7 carbons,

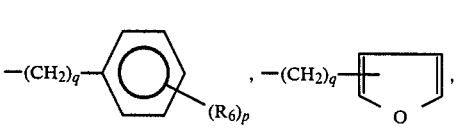

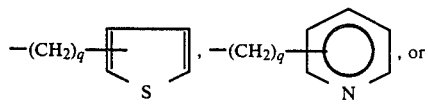

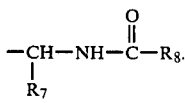

s is an integer from 1 to 7.

q is zero or an integer from 1 to 7.

$R_6$ is hydrogen, alkyl of 1 to 4 carbons, alkoxy of 1 to 4 carbons, alkylthio of 1 to 4 carbons, Cl, Br, F, CF$_3$, or hydroxy.

p is one, two or three provided that p is more than one only if $R_6$ is hydrogen, methyl, methoxy, Cl or F.

$R_3$ is hydrogen, straight or branched chain alkyl of 1 to 7 carbons, —(CH$_2$)$_r$—halo wherein halo is Cl, Br, or F, —CF$_3$,

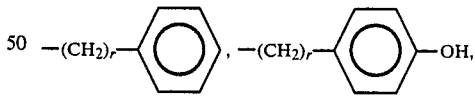

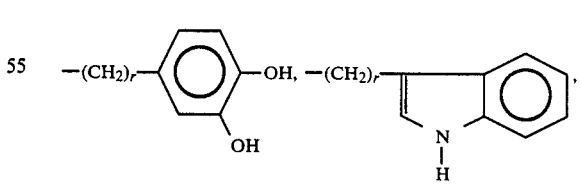

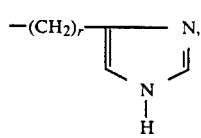

—(CH$_2$)$_r$—NH$_2$, —(CH$_2$)$_r$—SH, —(CH$_2$)$_r$—S—alkyl wherein alkyl is of 1 to 4 carbons,

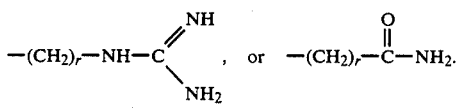

r is an integer from 1 to 4.

$R_7$ and $R_8$ are independently selected from hydrogen, straight or branched chain alkyl of 1 to 7 carbons, —$(CH_2)_s$—halo wherein halo is Cl, Br, or F,

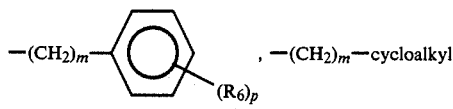

wherein cycloalkyl is a saturated ring of 4 to 7 carbons,

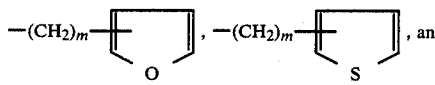

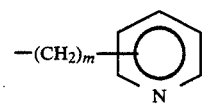

m is zero, one, two, or three.

$R_4$ and $R_5$ are easily removable ester protecting groups such as methyl and benzyl.

In the above reactions, if $R_3$ is

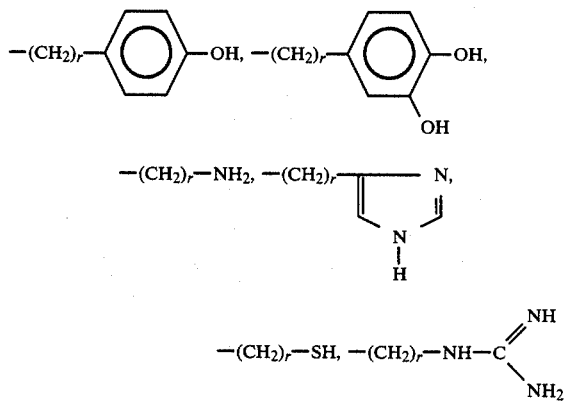

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Similarly, if $R_2$ is —$(CH_2)_s$—$NH_2$ in the above reactions then the amino group should be similarly protected, preferably by phthalidyl. This protecting group is removed by treatment with hydrazine following completion of the reaction.

As shown above, the proline portion of the molecule of the products of formula VI and I is in the L-configuration. Depending upon the definition of $R_3$ and $R_7$ other asymmetric centers may be present in the phosphonyl sidechain. The above described processes can utilize racemates, enantiomers or diastereomers as starting materials. When diastereomeric products are prepared, they can be separated by conventional chromatographic or fractional crystallization methods. As shown above, the asymmetric center in the sidechain of the orally active compounds of formula I is in the (S) configuration.

The final products of formula VI, including those of formula I, can be converted to the corresponding disalt compound by treating the diacid with a suitable salt forming reagent. Suitable disalt compounds include the pharmaceutically acceptable salts such as sodium, potassium, lithium, and calcium. Thus, the diacid product can be treated with lithium hydroxide, sodium hydroxide, potassium hydroxide, or calcium hydroxide to give the desired disalt product.

As set forth by Karanewsky, et al. in U.S. Pat. No. 4,452,790, the final products of formula VI including pharmaceutically acceptable salts thereof are useful as antihypertensive agents. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The final products of formula VI intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the final products of formula VI angiotensin dependent hypertension in a species of mammal (e.g., humans) suffering therefrom is alleviated.

In particular, it has been discovered that among the final products of formula VI those of formula I are especially useful as oral antihypertensive agents. The compounds of formula I have demonstrated a high level of bioavailability following oral administration to a test animal.

Accordingly, a single dose or two to four divided daily oral doses provided on a basis of from about 0.5 to about 10 mg. per kilogram of body weight per day of a compound of formula I is appropriate to reduce blood pressure.

The compounds of formula I can also be formulated with a diuretic for the treatment of hypertension. A combination products comprising a compound of formula I and a diuretic can be administered in an effective amount which comprises a totaly daily dosage of about 30 to 600 mg., preferably about 30 to 330 mg. of a compound of formula I, and about 15 to 300 mg. preferably about 15 to 200 of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendoflumethiazide, methylclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

Of course, the compounds of formula I can also be prepared according to the process in U.S. Pat. No. 4,452,790.

The following examples are illustrative of the invention. Temperatures are given in degrees Centigrade.

EXAMPLE 1

(S)-1-[6-Amino-2-[[hydroxy(2-phenylethyl)phosphinyl]oxy]-1-oxohexyl]-L-proline, dilithium salt

(a)

(S)-6-Amino-2-hydroxyhexanoic acid

An aqueous solution of L-lysine, monohydrochloride (18.3 g., 0.1 mole) is passed through an AG 3-X4A (100–200 mesh) ion exchange column (OH form, 500 ml. bed volume) eluting with water. The ninhydrin positive fractions are combined, acidified with 2M (4N) sulfuric acid (100 ml., 0.2 mole) and evaporated to dryness.

The crude L-lysine, disulfuric acid salt is taken up in 10% sulfuric acid (250 ml.) and treated dropwise with a solution of sodium nitrite (25.9 g., 0.36 mole) in water (100 ml.) at 45°–50° (bath temperature) over a period of 2 hours. When the addition is complete, the mixture is stirred at 45°–50° for an additional 4.5 hours, the excess nitrous acid decomposed with urea and the mixture is poured onto an AG-50-X8 ion exchange column (H+ form, 200 ml. bed volume). The column is eluted with water and then aqueous ammonia (concentrated ammonia-water, 1:3) to elute the product. The ninhydrin positive fractions are combined and evaporated to give a pink semi-solid which is recrystallized from water-ethanol to give 8.20 g. of (S)-6-amino-2-hydroxyhexanoic acid as white crystals; m.p. 197°–199°; $[\alpha]_D^{22} = -12.2°$ (c=1.2, water). TLC (silica gel; isopropanol: concentrated ammonia:water, 7:2:1) $R_f = 0.16$ (contains trace of lysine, $R_f = 0.22$).

(b)

(S)-6-[[(Phenylmethoxy)carbonyl]amino]-2-hydroxyhexanoic acid

A solution of (S)-6-amino-2-hydroxyhexanoic acid (7.5 g., 51.0 mmole) in 1N sodium hydroxide solution (50 ml.) at 0° (ice-bath) is adjusted to pH 10.0 with concentrated hydrochloric acid and treated with benzyl chloroformate (8.4 ml., 95%, 55.9 mmole) in approximately 1 ml. portions at 15 minute intervals. Throughout the reaction, the pH is maintained at pH 9.8–10.2 by the addition of 1N sodium hydroxide solution. When the addition is complete and the pH stabilized, the mixture is stirred at pH 10, 0°, for an additional 45 minutes, and then washed with one portion of ethyl ether. The aqueous solution is acidified to pH 1 with concentrated hydrochloric acid and extracted with ethyl acetate. The ethyl acetate extract is washed with saturated sodium chloride solution, dried over sodium sulfate, and evaporated. The residue is crystallized from isopropyl ether to give 13.5 g. of crude product as a white solid. Recrystallization of the crude product from ethyl acetate-hexane gives 11.48 g. of (S)-6-[[(phenylmethoxy)carbonyl]amino]-2-hydroxyhexanoic acid as a white crystalline solid; m.p. 79°–81°; $[\alpha]_D^{22} = +4.5°$, $[\alpha]_{365} = +26.8°$ (c=1.1, chloroform). TLC (silica gel; acetic acid:methanol:methylene chloride, 1:1:20) $R_f = 0.19$.

(c)

1-[(S)-6-[[(Phenylmethoxy)carbonyl]amino]-2-hydroxy-1-oxohexyl]-L-proline, phenylmethyl ester A mixture of (S)-6-[[(phenylmethoxy)carbonyl]amino]-2-hydroxyhexanoic acid (1.4 g., 5.0 mmole), L-proline, phenylmethyl ester, monohydrochloride (1.33 g., 5.5 mmole), and triethylamine (0.76 ml., 5.5 mmole) in dry tetrahydrofuran (15 ml.) at 0° (ice-bath) is treated with 1-hydroxybenzotriazole hydrate (0.71 g., 5.26 mmole) and dicyclohexylcarbodiimide (1.08 g., 5.23 mmole). The solution is stirred at 0° for 3 hours, then allowed to warm to room temperature and stirred for an additional one hour. The mixture is filtered, diluted with ethyl acetate, and washed successively with 5% potassium bisulfate, saturated sodium bicarbonate, and saturated sodium chloride, dried over sodium sulfate, and evaporated. The residue is taken up in carbon tetrachloride, filtered to remove the last traces of dicyclohexyl urea, and evaporated. The crude product is purified by flash chromatography on silica gel (35 g., Whatman LPS-1) eluting with ethyl acetate-hexane (2:1) to give 2.24 g. of 1-[(S)-6-[[(phenylmethoxy)carbonyl]amino]-2-hydroxy-1-oxohexyl]-L-proline, phenylmethyl ester as a colorless, very viscous oil. TLC (silica gel; methanol:methylene chloride, 5:95) $R_f = 0.36$.

(d)

(2-Phenylethyl)phosphonic acid, dibenzyl ester

Dibenzylphosphite (11.93 ml., 54 mmole, 1 eq.) is added dropwise to a stirred suspension of prewashed sodium hydride (1.45 g., 59.4 mmole, 1.1 eq.) in dry dimethylformamide (40 ml.) under argon at room temperature. After 1.5 hours, the brown homogeneous mixture is treated with phenethyl bromide (7.38 ml., 54 mmole, 1 eq.) and then stirred for 20 minutes. The mixture is then partitioned between 5% potassium bisulfate and ethyl acetate, the organic layer is washed with brine, dried over anhydrous sodium sulfate, and evaporated to a viscous yellow oil (20.6 g.). The crude oil is flash chromatographed (LPS-1 silica gel) eluting with hexane-ethyl acetate (7:3). Product containing fractions are pooled and evaporated to give 12.6 g. of (2-phenylethyl)phosphonic acid, dibenzyl ester as a clear, colorless oil. TLC (silica gel; petroleum ether:ethyl ether, 1:1) $R_f = 0.11$.

(e)

1-[(S)-2-[[(2-Phenylethyl)(phenylmethoxy)phosphinyl]oxy]-6-[[(phenylmethoxy)carbonyl]amino]-1-oxohexyl]-L-proline, phenylmethyl ester A mixture of (2-phenylethyl)phosphonic acid, dibenzyl ester (1.48 g., 4.04 mmole, 1.5 eq.) in dry benzene (15 ml.) is treated with phosphorus pentachloride (952 mg., 4.57 mmole, 1.7 eq.) and the solution is heated at 75° (oil bath) for 2.5 hours under argon. The mixture is evaporated to dryness (0.5 mm of Hg.), taken up in benzene (10 ml.), and evaporated. This procedure is repeated twice. The clear residue is taken up in dry methylene chloride (15 ml.), 1-[(S)-6-[[(phenylmethoxy)carbonyl]amino]-2-hydroxy-1-oxohexyl]-L-proline, phenylmethyl ester (1.26 g., 2.69 mmole, 1.0 eq.) is added, the mixture is cooled to 0° (ice-bath), then treated with triethylamine (0.56 ml., 4.04 mmole, 1.5 eq.) and dimethylaminopyridine (49 mg., 0.40 mmole, 0.15 eq.), stirred at 0° for 15 minutes, and then at room temperature for one hour. The mixture is partitioned between 5% potassium bisulfate and methylene chloride. The organic layer is washed with brine, dried over anhydrous sodium sulfate, and evaporated to a yellow oil. The crude oil is purified by flash chromatography (LPS-1 silica gel) eluting with hexane:acetone (7:3). Product containing fractions are pooled and evaporated to give 916 mg. of 1-[(S)-2-[[(2-phenylethyl)(phenylmethoxy)phosphinyl]oxy]-6-[[((phenylmethoxy)carbonyl]amino]-1-oxohexyl]-L-proline, phenylmethyl ester as a clear, colorless oil.

(f)

(S)-1-[6-Amino-2-[[hydroxy(2-phenylethyl)phosphinyl]oxy]-1-oxohexyl]-L-proline, dilithium salt An argon purged solution of the phenylmethyl ester product from part (e) (916 mg., 1.26 mmole) in a mixture of methanol (10 ml.), triethylamine (0.53 ml., 3.78 mmole, 3 eq.), and water (1.5 ml.) is treated with 10% palladium on carbon catalyst (184 mg., 20% by weight) and the black suspension is stirred under hydrogen for 5 hours. The catalyst is removed by filtration through Celite. The filtrate is evaporated, taken up in water, filtered through a polycarbonate filter and prefilter, evaporated again, taken up in 1N lithium hydroxide (5 ml.), and chromatographed on HP-20 resin (porous cross-linked polystyrene-divinyl benzene polymer resin) eluting with water→acetonitrile gradient system. Product containing fractions are pooled, evaporated, taken up in water (50 ml.), frozen, and lyophilized to give 373 mg. of (S)-1-[6-amino-2-[[hydroxy(2-phenylethyl)phosphinyl]oxy]-1-oxohexyl]-L-proline, dilithium salt as an off-white, granular solid; m.p. softens at 180°, melts at greater than 200°; $[\alpha]_D^{22} = -43°$ (c=0.5, methanol). TLC (silica gel; isopropanol:ammonia:water, 7:2:1) $R_f=0.17$.

Anal. calc'd for $C_{19}H_{27}N_2O_6P.2Li.1.12H_2O$: C, 51.35; N, 6.63; N, 6.30; P, 6.97. Found: C, 51.35; N, 6.75; N, 5.90; P, 6.80.

EXAMPLE 2

(S)-1-[6-Amino-2-[[hydroxy(3-phenylpropyl)phosphinyl]oxy]-1-oxohexyl]-L-proline (a)

(3-Phenylpropyl)phosphinic acid, 1-adamantanamine salt 2,2'-Azobisisobutyronitrile (3 g.) is added to a stirred mixture of 3-phenyl-1-propene (22.3 g., 188.7 mmole), sodium hypophosphite (60 g., 566 mmole, 3 eq.) in absolute ethanol (600 ml.), and concentrated sulfuric acid (15 ml.). The white suspension is refluxed for 3 hours, additional 2,2'-azobisisobutyronitrile (2 g.) is added, and the mixture is refluxed for 16 more hours. The cooled mixture is filtered, rinsed with ethanol, and evaporated to an oil. The resulting oil is taken up in water (100 ml.), made basic (pH of approximately 13) by the addition of 50% sodium hydroxide (about 25 ml.), cooled, and then extracted with ethyl ether (2×100 ml.). The aqueous layer is acidified with concentrated sulfuric acid (12 ml.) and extracted with ethyl acetate. The ethyl acetate extract is washed with brine, dried over anhydrous sodium sulfate, and evaporated to give 31.55 g. of crude (3-phenylpropyl)phosphinic acid as a clear oil.

This crude acid (18.4 g., 99.4 mmole) is taken up in ethyl ether (30 ml.) and adamantanamine (15.1 g., 100 mmole) in ethyl ether (60ml.) is added. The prrecipitate is collected by filtration, rinsed with ethyl ether, and dried in vacuo to give 29.7 g. of (3-phenylpropyl)phosphinic acid, 1-adamatanamine salt as a white, crystalline solid; m.p. 204°-207°. TLC (silica gel; isopropanol:ammonia:water, 7:2:1) $R_f=0.62$.

(b)

1-[(S)-6-[[(Phenylmethoxy)carbonyl]amino]-2-[[(3-phenylpropyl)phosphinyl]oxy]-1-oxohexyl]-L-proline, phenylmethyl ester (3-Phenylpropyl)phosphinic acid is regenerated from the 1-adamantanamine salt (1.61 g., 4.82 mmole) by dissolving the salt in 0.1N hydrochloric acid (50 ml.) and extracting with ethyl acetate. The organic layer is washed with brine, dried over anhydrous sodium sulfate, and evaporated to a clear oil. This oil is dissolved in dry tetrahydrofuran (20 ml.) and treated with 1-[(S)-6-[[(phenylmethoxy)carbonyl]amino]-2-hydroxy-1-oxohexyl]-L-proline, phenylmethyl ester (1.5 g., 3.21 mmole) followed by dicyclohexylcarbodiimide (995 mg., 4.82 mmole) and dimethylaminopyridine (59 mg.). After 5 hours at room temperature, the mixture is diluted with ethyl acetate, dicyclohexyl urea is filtered off, and the filtrate is washed with 5% potassium bisulfate, saturated sodium bicarbonate, and brine, dried over anhydrous sodium sulfate, and evaporated to an oil. This oil is taken up in ethyl acetate, filtered, evaporated, taken up in a minimum amount of ethyl acetate and chromatographed (SiliCAR CC-7 silica gel) eluting with acetone:hexane (1:1). Product containing fractions are pooled, evaporated, taken up in ethyl acetate, filtered, and evaporated to give 2.052 g. 1-[(S)-6-[[(phenylmethoxy)carbonyl]amino]-2-[[(3-phenylpropyl)phosphinyl]oxy]-1-oxohexyl]-L-proline, phenylmethyl ester as a clear oil. TLC (silica gel; acetone:hexane, 1:1) $R_f=0.30$.

(c)

1-[(S)-6-[[(Phenylmethoxy)carbonyl]amino]-2-[[hydroxy(3-phenylpropyl)phosphinyl]oxy]-1-oxohexyl]-L-proline, phenylmethyl ester, 1-adamantanamine salt A mixture of the phenylmethyl ester product from part (b) (2.052 g., 3.23 mmole) in dioxane (12 ml.) is treated with an aqueous medium periodate solution (794 mg., 3.71 mmole, 1.15 eq. in 4 ml. of water). The white suspension is stirred overnight under argon. The resulting orange suspension is partitioned between ethyl acetate and 10% potassium bisulfate. The organic phase is washed with water, dilute sodium bisulfite and brine, dried over anhydrous sodium sulfate, and evaporated to a yellow semi-solid. The solid is taken up in ethyl acetate, filtered, evaporated, taken up in ethyl acetate (2 ml.) and ethyl ether (5 ml.), and treated with an ethereal solution of adamantanamine (600 mg., in 5 ml. of ethyl ether). The precipitate is collected by filtration under a blanket of argon (hygroscopic solid), then dried in vacuo to give 1.857 g. of 1-[(S)-6-[[(phenylmethoxy)carbonyl]amino]-2-[[hydroxy(3-phenylpropyl)phosphinyl]oxy]-1-oxohexyl]-L-proline, phenylmethyl ester, 1-adamantanamine salt as a white solid. TLC (silica gel; methylene chloride:methanol:acetic acid, 20:1:1) $R_f=0.14$.

(d)

(S)-1-[6-Amino-2-[[hydroxy(3-phenylpropyl)phosphinyl]oxy]-1-oxohexyl]-L-proline The 1-adamantanamine salt product from part (c) (1.857 g.) is dissolved in 1.0N hydrochloric acid and extracted with ethyl acetate. The organic layer is washed with brine, dried over anhydrous sodium sulfate, and evaporated to give 1-[(S)-6-[[(phenylmethoxy)carbonyl]amino]-2-[[hydroxy(3-phenylpropyl)phosphinyl]oxy]-1-oxohexyl]-L-proline, phenylmethyl ester as a clear oil. An argon purged solution of this material in methanol (10 ml.) is treated with 10% palladium on carbon catalyst (226 mg., 15% by weight) and the black suspension is stirred under hydrogen for 1.5 hours. Catalyst is removed by filtration through dry, packed Celite. The residue is taken up in water (50 ml.), filtered through a polycarbonate membrane, and evaporated to give 963 mg. of (S)-1-[6-amino-2-[[hydroxy(3-phenylpropyl)phosphinyl]oxy]-1-oxohexyl]-L-proline as a white solid; m.p. 165°–175° with yellowing; $[\alpha]_D^{22} = -45.2°$ (c=0.5, methanol). TLC (silica gel; isopropanol:ammonia:water, 7:2:1) $R_f = 0.22$.

Anal. calc'd. for $C_{20}H_{31}N_2O_6P \cdot 1.42H_2O$: C, 53.13; H, 7.55; N, 6.20; P, 6.85. Found: C, 53.13; H, 7.31; N, 5.97; P, 6.90.

EXAMPLE 3

(S)-1-[6-Amino-2-[[hydroxy(4-phenylbutyl)phosphinyl]oxy]-1-oxohexyl]-L-proline, dilithium salt (a)

(4-Phenylbutyl)phosphonic acid, dibenzyl ester

Sodium hydride 50% oil dispersion (1.01 g., 20.8 mmole) is added to a solution of dibenzylphosphite (5.25 g., 20.0 mmole) in dry dimethylformamide (30 ml.) under argon. The resulting mixture is stirred at room temperature for one hour and at 40° (bath temperature) for 30 minutes. The resulting clear, yellow solution is allowed to cool to room temperature and treated with a solution of 4-phenylbutyl chloride (4.0 g., 23.7 mmole) in dimethylformamide (3 ml.). The resulting mixture is stirred at room temperature for 18 hours and at 40° for 2 hours. The mixture is partitioned between ethyl acetate-1% potassium bisulfate. The organic phase is washed successively with water (twice), saturated sodium bicarbonate (twice), and saturated sodium chloride (twice), dried over sodium sulfate, and evaporated. The residue is purified by flash chromatography (silica gel, 100 g. of LPS-1) eluting with ethyl acetate:hexane (3:7) to give (4-phenylbutyl)phosphonic acid, dibenzyl ester as a colorless, somewhat viscous oil.

(b)

1-[(S)-2-[[(4-phenylbutyl)(phenylmethoxy)phosphinyl]oxy]-6-[[(phenylmethoxy)carbonyl]amino]-1-oxohexyl]-L-proline, phenylmethyl ester Phosphorus pentachloride (320 mg., 1.54 mmole) is added to a solution of (4-phenylbutyl)phosphonic acid, dibenzyl ester (595 mg., 1.51 mmole) in dry benzene (3.0 ml.). The resulting mixture is stirred at room temperature under argon for 30 minutes and at 60° (bath temperature) for 45 minutes. The solution is evaporated (60°, 0.5 mm. of Hg.), taken up in benzene, and evaporated again. This procedure is repeated twice again. The crude phosphonochloridate is taken up in dry methylene chloride (5.0 ml.), treated with a solution of 1-[(S)-6-[[(phenylmethoxy)carbonyl]amino]-2-hydroxy-1-oxohexyl]-L-proline, phenylmethyl ester (0.72 g., 1.54 mmole) in dry methylene chloride (50 ml.), triethylamine (0.35 ml., 2.53 mmole), and dimethylaminopyridine (40 mg.), and stirred at room temperature under argon. After 4 hours, the mixture is partitioned between ethyl acetate-5% potassium bisulfate. The organic phase is washed successively with 5% potassium bisulfate, saturated sodium bicarbonate, and saturated sodium chloride, dried over anhydrous sodium sulfate, and evaporated. This crude product is again treated with a second batch of phosphonochloridate under the same conditions described above. Workup as before and purification by flash chromatography (silica gel, 100 g. of LPS-1) eluting with acetonehexane (3:7) gives 428 mg. of 1-[(S)-2-[[(4-phenylbutyl)(phenylmethoxy)phosphinyl]oxy]-6-[[(phenylmethoxy)carbonyl]amino]-1-oxohexyl]-L-proline, phenylmethyl ester as a viscous oil. TLC (silica gel; methanol:methylene chloride, 5:95) $R_f = 0.45$. TLC(silica gel; acetone:methylene chloride, 2:8) shows two spots (isomers at phosphorus, approximately 1:1) $R_f = 0.54$ and 0.49.

(c)

(S)-1-[6-Amino-2-[[hydroxy(4-phenylbutyl)phosphinyl]oxy]-1-oxohexyl]-L-proline, dilithium salt A solution of the phenylmethyl ester product from part (b) (428 mg., 0.57 mmole) in a mixture of methanol (15 ml.), water (3 ml.), and triethylamine (0.27 ml.) is treated with 10% palladium on carbon catalyst (10 g.) and stirred under an atmosphere of hydrogen (balloon) for 3 hours. The mixture is filtered through Celite and the catalyst is washed thoroughly with methanol. The combined filtrates are treated with 2N lithium hydroxide solution (0.85 ml., 1.7 mmole) and evaporated to dryness. The residue is taken up in water, filtered (Millipore), and lyophilized. The crude product is purified on an HP-20 column (250 ml. bed volume, 1 inch diameter column) eluting with a gradient of water→acetonitrile (90%) at a flow rate of 5 ml./minute collecting 5 ml. fractions. The product containing fractions are combined and evaporated to dryness. The residue is taken up in water, filtered (Millipore), and lyophilized to give 215 mg. of (S)-1-[6-amino-2-[[hydroxy(4-phenylbutyl)phosphinyl]oxy]-1-oxohexyl]-L-proline, dilithium salt as a white solid; $[\alpha]_D^{22} = -41.4°$ (c=1.15, methanol). TLC (silica gel; isopropanol:concentrated ammonia:water, 7:2:1) $R_f = 0.33$.

Anal. calc'd for $C_{21}H_{31}N_2O_6P \cdot 2Li \cdot 1.3H_2O$: C, 53.01; H, 7.12; N, 5.89; P, 6.51. Found: C, 52.97; H, 7.35; N, 5.74; P, 6.2.

EXAMPLE 4

(S)-1-[6-Amino-2-[[hydroxy(4-phenylbutyl)phosphinyl]-oxy]-1-oxohexyl]-L-proline (a)

(4-Phenylbutyl)phosphinic acid

To a suspension of sodium hypophosphite hydrate (60 g., 0.566 mmole) is absolute ethanol (600 ml.) is added concentrated sulfuric acid (15 ml.), 4-phenyl-1-butene (25.0 g., 0.189 mmole) and 2,2'-azobisisobutyronitrile (3.0 g.). The resulting mixture is refluxed for 6 hours, treated with a second portion of 2,2'-azobisisobutyronitrile (2.0 g.), and refluxed for an additional 16 hours. The cooled mixture is filtered and concentrated in vacuo. The residue is suspended in water (200 ml.), made basic with 50% sodium hydroxide solution, and washed with two portions of ethyl ether (200 ml. each). The aqueous phase is acidified with concentrated sulfuric acid and extracted with ethyl acetate. The ethyl acetate extract is washed with saturated sodium chloride, dried over anhydrous sodium sulfate, and evaporated to give 34.5 g. of crude (4-phenylbutyl)phosphinic acid.

This crude acid (34.5 g.) is taken up in ethyl ether (200 ml.) and treated with a solution of 1-adamantanamine (26.3 g., 0.174 mmole) in ethyl ether (200 ml.). The white precipitate is collected, washed with ethyl ether, and dried in vacuo to give 54.2 g. of (4-phenylbutyl)phosphinic acid, 1-adamantanamine salt as a white solid; m.p. 192°-200°.

This 1-adamantanamine salt (10.5 g.) is partitioned between ethyl acetate −1N hydrochloric acid (150 ml. each). The ethyl acetate phase is washed with 1N hydrochloric acid and saturated sodium chloride, dried over anhydrous sodium sulfate, and evaporated to give 5.75 g. of pure (4-phenylbutyl)phosphinic acid as a colorless, viscous oil. TLC (silica gel; isopropanol:concentrated ammonia:water, 7:2:1) $R_f=0.67$.

(b)

1-[(S)-6-[[(Phenylmethoxy)carbonyl]amino]-2-[[hydroxy(4-phenylbutyl)phosphinyl]oxy]-1-oxohexyl]-L-proline, phenylmethyl ester, 1-adamantanamine salt A solution of (4-phenylbutyl)phosphinic acid (0.67 g., 3.38 mmole) and 1-[(S)-6-[[(phenylmethoxy)carbonyl]amino]-2-hydroxy-1-oxohexyl]-L-proline, phenylmethyl ester (1.0 g., 2.14 mmole) in dry tetrahydrofuran (8.0 ml.) is treated with dicyclohexylcarbodiimide (0.67 g., 3.25 mmole) and dimethylaminopyridine (0.1 g.) and stirred at room temperature under argon. After 2 hours, the mixture is filtered, diluted with ethyl acetate, and washed successively with 5% potassium bisulfate, saturated sodium bicarbonate, and saturated sodium chloride solution, dried over anhydrous sodium sulfate, and evaporated. The residue is filtered through a pad of silica gel (SiliCAR CC7, 10 g.) eluting with acetone:hexane (1:1). The product containing fractions are pooled and evaporated to give 1.42 g. of 1-[(S)-6-[[(phenylmethoxy)carbonyl]amino]-2-[[(4-phenylbutyl)phosphinyl]oxy]-1-oxohexyl]-L-proline, phenylmethyl ester as a colorless oil. TLC (silica gel; acetone:hexane, 1:1) $R_f=0.18$.

The above phenylmethyl ester (1.42 g) is taken up in dioxane (10 ml.), treated with a solution of sodium periodate (0.5 g., 2.34 mmole) in water (6 ml.), and stirred at room temperature for 16 hours. The orange mixture is then partitioned between ethyl acetate −1% potassium bisulfate solution. The organic phase is washed with water, dilute sodium bisulfite, and saturated sodium chloride, dried over anhydrous sodium sulfate, and evaporated. The crude product is taken up in a small amount of ethyl acetate (about 5 ml.), diluted with ethyl ether (about 20 ml.), and treated with a solution of 1-adamantanamine (0.34 g., 2.25 mmole) in ethyl ether (4 ml.). The white precipitate is collected, washed with ethyl ether, and dried in vacuo to give 1.5 g. of 1-[(S)-6-[[(phenylmethoxy)carbonyl]amino]-2-[[hydroxy(4-phenylbutyl)phosphinyl]oxy]-1-oxohexyl]-L-proline, phenylmethyl ester, 1-adamantanamine salt as a white solid; m.p. 129°-140°. TLC (silica gel; acetic acid:methanol:methylene chloride; 1:1:20) $R_f=0.24$ (free acid).

(c)

(S)-1-[6-Amino-2-[[hydroxy(4-phenylbutyl)phosphinyl]oxy]-1-oxohexyl]-L-proline

The 1-adamantanamine salt product from part (b) (0.8 g., 0.98 mmole) is partitioned between ethyl acetate and 1N hydrochloric acid (20 ml. each). The ethyl acetate layer is washed with 1N hydrochloric acid and saturated sodium chloride solutions, dried over anhydrous sodium sulfate, and evaporated. The residue is taken up in methanol (8.0 ml.), treated with 10% palladium on carbon catalyst (0.1 g.), and stirred under an atmosphere of hydrogen (balloon) for 1.5 hours. The mixture is filtered through Celite and evaporated to dryness. The residue is taken up in water and filtered through a polycarbonate filter to remove traces of dicyclohexylurea. Evaporation of the eluent gives 0.41 g. of (S)-1-[6-amino-2-[[hydroxy(4-phenylbutyl)phosphinyl]oxy]-1-oxo-hexyl]-L-proline as a white solid; m.p. 160°-175° after trituration from acetonitrile. Material crystallized from water-acetonitrile m.p. 187°-192° (decomposition); $[\alpha]_D^{22}=-46.7°$ (c=5.05, methanol). TLC (silica gel; isopropanol:ammonia:water, 7:2:1) $R_f=0.24$.

Anal. calc'd for $C_{21}H_{33}N_2O_6P \cdot 0.7H_2O$: C, 55.67; H, 7.65; N, 6.18; P, 6.84, Found: C, 55.67; H, 7.76; N, 6.28; P, 6.55.

EXAMPLE 5

(S)-1-[6-Amino-2-[[[4-(4-fluorophenyl)butyl]-hydroxyphosphinyl]oxy]-1-oxohexyl]-L-proline (a)

4-Fluorophenyl-1-butene

A stirred suspension of magnesium turnings (8.41 g., 346 mmole) and a small iodine crystal in distilled ethyl ether (400 ml.) is treated with a small quantity of a 4-fluorobenzyl chloride solution (41.4 ml., 50 g., 346 mmole in 100 ml. of dry ethyl ether). The mixture is heated at 40° (warm bath) until a reaction is initiated and addition is continued dropwise thereafter to maintain constant boiling. After completed chloride addition, the mixture is refluxed for 15 minutes, cooled and treated with a small quantity of allyl bromide (60 ml., 692 mmole, 2 eq.) until reaction (boiling) is again initiated. Dropwise addition of the bromide is continued so as to maintain a gentle reflux and a creamy white precipitate is observed. After the bromide addition is completed, the mixture is filtered through dry, packed Celite, washed (three times) with ammonium chloride and brine, and then dried over anhydrous potassium carbonate. Excess ethyl ether is removed by distillation at atmospheric pressure and the remaining residue is distilled in vacuo to give 40.015 g. of 4-fluorophenyl-1-butene as a clear, colorless liquid; b.p. 57°-58° (8-9 mm. of Hg.).

(b)

[4-(4-Fluorophenyl)butyl]phosphinic acid, 1-adamantanamine salt

A mixture of 4-fluorophenyl-1-butene (28.4 g.) and sodium hypophosphite hydrate (60 g.) in absolute ethanol (600 ml.) and concentrated sufuric acid (15 ml.) is treated with 2,2'-azobisisobutyronitrile (3 g.) and refluxed for 4 hours. Additional 2,2'-azobisisobutyronitrile (2 g.) is then added and the white suspension is refluxed overnight. The suspension is filtered, the filtrate is evaporated, taken up in water (100 ml.), made basic with 50% sodium hydroxide solution (25 ml.), and extracted with ethyl ether (twice). The aqueous layer is carefully acidified with concentrated sulfuric acid (12 ml.) and extracted with ethyl acetate (twice). The organic phase is washed with brine, dried over anhydrous sodium sulfate, and evaporated to give 36.2 g. of [4-(4-fluorophenyl)butyl]phosphinic acid as a pale yellow oil.

A portion of this crude acid (10 g.) is dissolved in ethyl ether (25 ml.) and treated with an ethereal solution of 1-adamantanamine (7 g. in 50 ml. of ethyl ether). The precipitate is collected by filtration, rinsed with ethyl ether, and dried in vacuo to give 14.414 g. of [4-(4-fluorophenyl)butyl]phosphinic acid, 1-adamantanamine salt as a white crystalline solid; m.p. 191°–194°. TLC (silica gel; isopropanol:ammonia:water, 7:2:1) $R_f=0.57$.

(c)

1-[(S)-6-[[(Phenylmethoxy)carbonyl]amino]-2-[[[4-(4-fluorphenyl)butyl]phosphinyl]oxy]-1-oxohexyl]-L-proline, phenylmethyl ester

[4-(4-Fluorophenyl)butyl]phosphinic acid, 1-adamantanamine salt (1.18 g.) is partitioned between 1.0N hydrochloric acid and ethyl acetate. The organic phase is washed with brine and dried over anhydrous sodium sulfate. The mixture is evaporated to give 696 mg. of [4-(4-fluorophenyl)butyl]phosphinic acid. This acid (696 mg., 3.22 mmole, 1.5 eq.) is dissolved in dry tetrahydrofuran (15 ml.), combined with 1-[(S)-6-[[(phenylmethoxy)carbonyl]amino]-2-hydroxy-1-oxohexyl]-L-proline, phenylmethyl ester (1.01 g., 2.15 mmole, 1 eq.) and treated with dicyclohexylcarbodiimide (664 mg., 3.22 mmole, 1.5 eq.) and dimethylaminopyridine (39 mg., 0.15 eq.). The white suspension is stirred under argon for 1 hour at room temperature, then diluted with ethyl acetate, and filtered to remove dicyclohexyl urea. The filtrate is washed with 5% potassium bisulfate, saturated sodium bicarbonate, and brine, then dried over anhydrous sodium sulfate, and evaporated to an oily residue. Chromatography on a ¾ inch pad of Sili-CAR CC-7 silica gel eluting with ethyl ether:acetone (8:2) removes impurities. Product containing fractions are pooled and evaporated to give crude 1-[(S)-6-[[(phenylmethoxy)carbonyl]amino]-2-[[[4-(4-fluorophenyl)butyl]phosphinyl]oxy]-1-oxohexyl]-L-proline, phenylmethyl ester as an oil. TLC (silica gel; ethyl ether:acetone, 8:2) $R_f=0.09$.

(d)

1-[(S)-6-[[(Phenylmethoxy)carbonyl]amino]-2-[[[4-(4-fluorophenyl)butyl]hydroxyphosphinyl]oxy]-1-oxohexyl]-L-proline, phenylmethyl ester A mixture of the crude phenylmethyl ester product from part (c) in dioxane (10 ml.) is treated with an aqueous sodium periodate solution (791 mg., 3.70 mmole, 1.15 eq. in 3.0 ml. of water) and the mixture is stirred overnight under argon. The yellow suspension is diluted with water, filtered, and then partitioned between 1% potassium bisulfate and ethyl acetate. The organic phase is washed with water, dilute sodium bisulfite (enough to discharge color) and brine, then dried over anhydrous sodium sulfate, and evaporated to an oil. A solution of the crude oil in ethyl ether (10 ml.) is treated with an ethereal solution of 1-adamantanamine (487 mg. in 5 ml. of ethyl ether). The precipitated salt is collected by filtration under argon and dried in vacuo. This salt is converted back to the free acid by partitioning between 1.0N hydrochloric acid and ethyl acetate, washing the organic phase with brine, drying over anhydrous sodium sulfate, and evaporating to give 1.25 g. of 1-[(S)-6-[[(phenylmethoxy)carbonyl]amino]-2-[[[4-(4-fluorophenyl)butyl]hydroxyphosphinyl]oxy]-1-oxohexyl]-L-proline, phenylmethyl ester as a pale yellow oil. TLC (silica gel; methylene chloride:methanol:acetic acid, 20:1:1) $R_f=0.62$.

(e)

(S)-1-[6-Amino-2-[[[4-(4-fluorophenyl)butyl]hydroxyphosphinyl]oxy]-1-oxohexyl]-L-proline 20% palladium over carbon catalyst (188 mg., 15% by weight) is added to an argon purged solution of the phenylmethyl ester product from part (d) (1.25 g.) in methanol (15 ml.). The black suspension is stirred under hydrogen for 45 minutes. The catalyst is removed by filtration through dry, packed Celite, and the filtrate is evaporated down to a 3–5 ml. volume. Water (50 ml.) is added and residual precipitated dicyclohexyl urea is removed by filtration through a polycarbonate membrane. Concentration in vacuo gives 788 mg. of (S)-1-[6-amino-2-[[[4-(4-fluorophenyl)butyl]hydroxyphosphinyl]oxy]-1-oxohexyl]-L-proline as a white solid; m.p. 178°–185° with yellowing; $[\alpha]^{22} = -41.8°$ (c=0.5, methanol). TCL (silica gel; isopropanol:ammonia:water, 7:2:1) $R_f=0.24$.

Anal. calc'd. for $C_{21}H_{32}N_2O_6F \cdot 1.6H_2O$: C, 51.76; H, 7.28; N, 5.75; F, 3.90; P, 6.36, Found: C, 51.79; H, 7.04; N, 5.36; F, 3.90; P, 6.40.

EXAMPLE 6

(S)-1-[6-Amino-2-[[hydroxy(5-phenylpentyl)phosphinyl]oxy]-1-oxyhexyl]-L-proline (a)

5-Phenyl-1-pentene

A suspension of pyridinium dichromate (37.6 g., 0.10 mole) in methylene chloride (150 ml.) is treated with 4-phenylbutanol (9.20 g., 61.2 mmole) and stirred at room temperature for 16 hours. The mixture was treated with an additional portion of pyridinium dichromate (10.0 g., 26.6 mmole) and stirred for an additional 6 hours. The mixture is then diluted with ethyl ether (about 200 ml.) and filtered through a layered pad of Celite over Florisil eluting with ethyl ether. Concentration of the filtrate gives 8.85 g. of crude 4-phenylbutanal. TLC (silica gel; ethyl acetate:hexane, 1:1) $R_f=0.74$.

A solution of 0.6M potassium hexamethyldisilazane in toluene (72.0 ml., 43.2 mmole) is added dropwise to a suspension of methyltriphenylphosphonium bromide (17.4 g., 48.7 mmole) in benzene (200 ml.) at room temperature under argon. After stirring at room temperature for 45 minutes, a solution of the crude aldehyde (8.85 g.) in benzene (10 ml.) is added dropwise and the resulting mixture is stirred at room temperature for 3 hours. The reaction mixture is then poured onto saturated ammonium chloride solution, washed successively with 5% potassium bisulfate and saturated sodium chloride solutions and dried over sodium sulfate. The solvents are removed by distillation at atmospheric pressure through a Vigreaux column. The residue is taken up in ethyl ether, the triphenylphosphine oxide is filtered off, and the filtrate is distilled in vacuo to give 4.71 g. of 5-phenyl-1-pentene as a colorless liquid; b.p. 90°–95° (20 mm. of Hg.).

(b)

(5-Phenylpentyl)phosphinic acid

A mixture of sodium hypophosphite hydrate (10.0 g., 94.3 mmole), concentrated sulfuric acid (2.5 ml.), and 5-phenyl-1-pentene (4.61 g., 31.6 mmole) in absolute ethanol (100 ml.) is treated with 2,2'-azobisisobutyronitrile (0.5 g.) and refluxed for 4 hours. The mixture is then treated with a second portion of 2,2'-azobisisobutronitrile (0.5 g.) and refluxed for an additional 16 hours. A third portion of 2,2'-azobisisobutyronitrile (0.5 g.) is added and reflux continued for 5 more hours.

The mixture is filtered and evaporated to dryness. The residue is suspended in water (approximately 100 ml.), made basic with 3N sodium hydroxide solution and washed with ethyl ether (2×100 ml.). The aqueous phase is acidified with 2M sulfuric acid and extracted with ethyl acetate. The ethyl acetate extract is washed with saturated sodium chloride solution, dried over anhydrous sodium sulfate, and evaporated to give 5.51 g. of crude (5-phenylpentyl)phosphinic acid as a viscous liquid. This crude acid is taken up in ethyl ether (approximately 50 ml.) and treated with a solution of 1-adamantanamine (4.0 g., 26.5 mmole) in ethyl ether (20 ml.). The white precipitate is collected, washed with ethyl ether, and dried in vacuo to give 7.73 g. of (5-phenylpentyl)phosphinic acid, 1-adamantanamine salt, m.p. 182°–184°, as a white solid. This 1-adamantanamine salt (2.0 g.) is partitioned between ethyl acetate and 1N hydrochloric acid. The organic phase is washed with 1N hydrochloric acid and saturated sodium chloride solutions, dried over anhydrous sodium sulfate, and evaporated to give 1.13 g. of pure (5-phenylpentyl)phosphinic acid as a colorless viscous liquid.

(c)

1-[(S)-6-[[(Phenylmethoxy)carbonyl]amino]-2-[[(5-phenylpentyl)hydroxyphosphinyl]oxy]-1-oxohexyl]-L-proline, phenylmethyl ester, 1-adamantanamine salt A mixture of (5-phenylpentyl)phosphinic acid (0.86 g., 4.06 mmole) and 1-[(S)-6-[[(phenylmethoxy)carbonyl]amino]-2-hydroxy-1-oxohexyl]-L-proline, phenylmethyl ester (1.2 g., 2.56 mmole) in dry tetrahydrofuran (5.0 ml.) is treated with dicyclohexylcarbodiimide (0.85 g., 4.13 mmole) and dimethylaminopyridine (0.10 g.) and stirred at room temperature under argon. After 3 hours, the mixture is diluted with ethyl acetate and filtered. The filtrate is washed successively with 5% potassium bisulfate, saturated sodium bicarbonate, and saturated sodium chloride solutions, dried over anhydrous sodium sulfate, and evaporated. The residue is taken up in ethyl acetate-hexane, filtered to remove dicyclohexyl urea, and again evaporated. The crude product is filtered through a silica gel pad (SiliCar CC-7) eluting with acetone:hexane (1:1) to remove polar impurities. TLC (silica gel; ethyl acetate:acetone, 8:2) $R_f=0.27$.

This purified 1-[(S)-6-[[(phenylmethoxy)carbonyl]amino]-2-[[(5-phenylpentyl)phosphinyl]oxy]-1-oxohexyl]-L-proline, phenylmethyl ester is taken up in dioxane (9 ml.) and treated with a solution of sodium periodate (0.63 g., 2.94 mmole) in water (5 ml.). The resulting mixture is stirred at room temperature under argon for 16 hours. The mixture is then partitioned between 1% potassium bisulfate and ethyl acetate. The organic phase is washed with dilute sodium bisulfite and saturated sodium chloride solutions, dried over anhydrous sodium sulfate, and evaporated. The crude product is taken up in a small amount of ethyl acetate (approximately 5 ml.), diluted with ethyl ether (approximately 50 ml.), and treated with a solution of 1-adamantanamine (0.4 g., 2.65 mmole) in ethyl ether (5 ml.). The mixture is evaporated to dryness and the solid residue triturated with ethyl ether-hexane to give 1.791 g. of 1-[(S)-6-[[(phenylmethoxy)carbonyl]amino]-2-[[(5-phenylpentyl)hydroxyphosphinyl]oxy]-1-oxohexyl]-L-proline, phenylmethyl ester, 1-adamantanamine salt as a white solid; m.p. 103°–105°. TLC (silica gel; acetic acid:methanol:methylene chloride, 1:1:20) $R_f=0.25$ (free acid).

(d)

(S)-1-[6-Amino-2-[[hydroxy(5-phenylpentyl)phosphinyl]oxy]-1-oxohexyl]-L-proline

The 1-adamantanamine salt product from part (c) (1.790 g., 21.6 mmole) is partitioned between ethyl acetate and 1N hydrochloric acid (approximately 50 ml. each). The ethyl acetate phase is washed with 1N hydrochloric acid and saturated sodium chloride solutions, dried over anhydrous sodium sulfate, and evaporated to give the phenylmethyl ester product as a viscous oil.

This phenylmethyl ester is taken up in methanol (12 ml.), treated with 10% palladium on carbon catalyst (0.2 g.), and stirred under an atmosphere of hydrogen (balloon) for 2 hours. An additional 20% palladium hydroxide carbon catalyst (0.16 g.) is added and the mixture is hydrogenated for an additional 2 hours. The mixture is filtered through Celite and evaporated. The residue is taken up in water with enough methanol to effect solution and the solution is filtered through a polycarbonate membrane. Evaporation of the filtrate gives 0.946 g. of (S)-1-[6-amino-2-[[hydroxy(5-phenylpentyl)phosphinyl]oxy]-1-oxohexyl]-L-proline as a white crystalline solid; m.p. shrinks at 140°, 145°–149°; $[\alpha]_D^{22}=-41.6°$ (c=0.65, methanol).

TLC (silica gel; isopropanol:concentrated ammonia:water, 7:2:1) $R_f=0.23$.

Anal. calc'd. for $C_{22}H_{35}N_2O_6P \cdot 1.5H_2O$: C, 54.87; H, 7.94; N, 5.82; P, 6.43, Found: C, 54.83; H, 7.54; N, 5.59; P, 6.20.

EXAMPLE 7

1-[(S)-6-Amino-2-[(hydroxypentylphosphinyl)oxy]-1-oxohexyl]-L-proline (a)

Pentylphosphinic acid

To a stirred suspension of sodium hypophosphite hydrate (56 g.) in absolute ethanol (500 ml.) is added concentrated sulfuric acid (14 ml.), then 1-pentene (11.9 g., 0.17 mole) and 2,2'-azobisisobutyronitrile (2.7 g.). The reaction flask is equipped with a dry ice condenser, and the reaction mixture is heated at reflux overnight. The cooled mixture is filtered through sintered glass, and the filtrate is concentrated in vacuo. The resulting clear oil is dissolved in water (100 ml.), made basic with 50% sodium hydroxide (pH 13), and washed with ethyl ether (2×100 ml.). The aqueous solution is acidified with concentrated sulfuric acid (pH 1.5) and the product is extracted with ethyl acetate (300 ml.). The organic phase is washed with brine, dried over anhydrous magnesium sulfate, and concentrated in vacuo to give 21.7 g. of pentylphosphinic acid as a clear, colorless oil.

(b)

1-[(S)-6-[[(Phenylmethoxy)carbonyl]amino]-2-[(pentylphosphinyl)oxy]-1-oxohexyl]-L-proline, phenylmethyl ester Pentylphosphinic acid (0.94 g., 6.9 mmole) is dissolved in tetrahydrofuran (30 ml.), 1-[(S)-6-[[(phenylmethoxy)carbonyl]amino]-2-hydroxy-1-oxohexyl]-L-proline, phenylmethyl ester (3.22 g., 6.0 mmole), dicyclohexylcarbodiimide (1.42 g., 6.0 mmole) and dimethylaminopyridine (0.15 g.) are added. The white suspension is stirred for 6 hours under argon at room temperature. The mixture is diluted with ethyl acetate (200 ml.), filtered and the filtrate is washed with 5% potassium bisulfate, saturated sodium bicarbonate, and brine, then dried over anhydrous sodium sulfate, and concentrated in vacuo to give 4.1 g. of crude 1-[(S)-6-[[(phenylmethoxy)carbonyl]amino]-2-[(pentylphosphinyl)oxy]-1-oxohexyl]-L-proline, phenylmethyl ester.

(c)

1-[(S)-6-[[(Phenylmethoxy)carbonyl]amino]-2-[(hydroxypentylphosphinyl)oxy]-1-oxohexyl]-L-proline, phenylmethyl ester A solution of the phenylmethyl ester product from part (b) in dioxane (45 ml.) is treated with a solution of sodium periodate (1.5 g., 7 mmole) in water (17 ml.). The resulting mixture is stirred under argon at room temperature overnight. The light brown solution is diluted with ethyl acetate (250 ml.) and washed sequentially with 10% potassium bisulfate (100 ml.), 40% sodium bisulfite (100 ml.), water, and brine, then dried over anhydrous magnesium sulfate, and concentrated in vacuo to give 4.3 g. of crude 1-[(S)-6-[[(phenylmethoxy)carbonyl]amino]-2-[(hydroxypentylphosphinyl)oxy]-1-oxohexyl]-L-proline, phenylmethyl ester.

This phenylmethyl ester (4.3 g.) is dissolved in ethyl acetate (20 ml.) and 1-adamantanamine (2.0 g.) in ethyl acetate (15 ml.) is added. The precipitated salt is collected to yield 5.0 g. of 1-[(S)-6-[[(phenylmethoxy)carbonyl]amino]-2-[(hydroxypentylphosphinyl)oxy]-1-oxohexyl]-L-proline, phenylmethyl ester, 1-adamantanamine salt as a white solid. This salt (5.0 g.) is partitioned between 1N hydrochloric acid and ethyl acetate. The organic phase is washed with brine, dried over anhydrous sodium sulfate, and concentrated in vacuo to give 2.8 g. of 1-[(S)-6-[[(phenylmethoxy)carbonyl]amino]-2-[(hydroxypentylphosphinyl)oxy]-1-oxohexyl]-L-proline, phenylmethyl ester.

(d)

1-[(S)-6-Amino-2-[(hydroxypentylphosphinyl)oxy]-1-oxohexyl]-L-proline

20% Palladium on carbon catalyst is added to a solution of the phenylmethyl ester product from part (c) in methanol (20 ml.) and the mixture is hydrogenated at atmospheric pressure for 45 minutes. The catalyst is removed by filtration through Celite and the filtrate is concentrated in vacuo. The residue is dissolved in water (10 ml.), filtered through a polycarbonate membrane, and the filtrate is concentrated to 3 ml. The product crystallizes slowly at 0° for 2 hours, and is then filtered and dried in vacuo to give 0.92 g. of 1-[(S)-6-amino-2-[(hydroxypentylphosphinyl)oxy]-1-oxohexyl]-L-proline as a white solid; m.p. 175°–179° (decomposition), $[\alpha]_D^{22} = -65°$ (c=0.51, methanol). TLC (silica gel; isopropanol:ammonia:water, 7:2:1) $R_f=0.24$.

Anal calc'd. for $C_{16}H_{31}N_2PO_2.1.2H_2O$: C, 48.04; H, 8.42; N, 7.00; P, 7.74. Found: C, 48.11; H, 8.39; N, 6.90; P, 7.45.

EXAMPLE 8

(S)-1-[6-Amino-2-[(hexylhydroxyphosphinyl)oxy]-1-oxohexyl]-L-proline, dilithium salt

(a)

Hexylphosphonic acid, dibenzyl ester

Dibenzyl phosphite (13.48 ml., 61 mmole) is added dropwise to a suspension of prewashed sodium hydride (1.61 g., 67.1 mmole) in dry dimethylformamide (45 ml.). The brown mixture is stirred for two hours at room temperature under argon. n-Hexyl bromide (8.5 ml., 60.6 mmole) is then added, the mixture is stirred for 30 minutes at room temperature, and then partitioned between 5% potassium bisulfate and ethyl acetate. The organic layer is washed with brine, dried over anhydrous sodium sulfate, and evaporated to a yellow oil which is flash chromatographed (LPS-1 silica gel) eluting with hexane:ethyl acetate (8:2). The product containing fractions are pooled and evaporated to give 9.33 g. of hexylphosphonic acid, dibenzyl ester as a clear, colorless oil.

(b)

1-[(S)-2-[[(Phenylmethoxy)hexylphosphinyl]oxy]-6-[[(phenylmethoxy)carbonyl]amino]-1-oxohexyl]-L-proline, phenylmethyl ester A solution of hexylphosphonic acid, dibenzyl ester (1.5 g., 4.5 mmole) in dry benzene (5 ml.) is treated with phosphorus pentachloride (0.95 g., 4.57 mmole) and heated at 70° (bath temperature) under argon for 1.5 hours. The solution is evaporated to dryness (0.5 mm of Hg., 70°) and the residue is taken up in benzene (approximately 3 ml.) and evaporated again.

The resulting crude phosphonochloridate is taken up in dry methylene chloride (10 ml.) and treated with a solution of 1-[(S)-6-[[(phenylmethoxy)carbonyl]amino]-2-hydroxy-1-oxohexyl]-L-proline, phenylmethyl ester (1.4 g., 3.0 mmole) in methylene chloride (5 ml.). The resulting solution is cooled in an ice bath, treated with triethylamine (0.83 ml., 6.0 mmole) and dimethylaminopyridine (0.1 g.), and allowed to warm to room temperature. After stirring for 2 hours at room temperature, the mixture is partitioned between ethyl acetate and 5% potassium bisulfate. The organic phase is washed successively with 5% potassium bisulfate, saturated sodium bicarbonate, and saturated sodium chloride solutions, dried over anhydrous sodium sulfate, and evaporated. The crude product is purified by flash chromatography on silica gel (LPS-1, 80 g.) eluting with acetone:hexane (3:7) then on neutral alumina (Act III, 60 g.) eluting with acetone:hexane (3:7) to give 0.95 g. of 1-[(S)-2-[[(phenylmethoxy)hexylphosphinyl]oxy]-6-[[(phenylmethoxy)carbonyl]amino]-1-oxohexyl]-L-proline, phenylmethyl ester as colorless, viscous oil. TLC (silica gel; acetone:methylene chloride, 2:8) two overlapping spots (isomeric at phosphorus) $R_f=0.69$ and 0.66.

(c)

(S)-1-[6-Amino-2-[(hexylhydroxyphosphinyl)oxy]-1-oxohexyl]-L-proline, dilithium salt A solution of the phenylmethyl ester product from part (b) (0.91 g., 1.29 mmole) in a mixture of methanol (30 ml.), water (6 ml.), and triethylamine (0.6 ml.) is treated with 10% palladium on carbon catalyst (0.2 g.) and stirred under an atmosphere of hydrogen (balloon) for 1.5 hours. The mixture is filtered through Celite and the catalyst is washed thoroughly with methanol. The combined filtrates are treated with 2N lithium hydroxide (1.9 ml., 3.8 mmole) and evaporated to dryness. The glassy residue is taken up in water, filtered (millipore), and chromatographed on an HP-20 column (250 ml. bed volume, 1 inch diameter) eluting with a gradient of water (100%)→acetonitrile (90%) at a flow of 5 ml./minute collecting 5 ml. fractions. The product containing fractions are combined and evaporated. The residue is taken up in water, filtered (millipore), and lyophilized to give 368 mg. of (S)-1-[6-amino-2-[(hexylhydroxyphosphinyl)oxy]-1-oxohexyl]-L-proline, dilithium salt as a white granular solid; m.p. 223°–226° (decomposition); $[\alpha]_D^{22} = -50.1°$ (c=1.12, methanol). TLC (silica gel; isopropanol:concentrated ammonia:water, 7:2:1) $R_f = 0.34$.

Anal. calc'd. for $C_{17}H_{31}N_2O_6P \cdot 2Li \cdot 0.38H_2O$: C, 49.67; H, 7.79; N, 6.83; P. 7.53. Found: C, 49.67; H, 8.16; N, 6.83; P. 7.1.

EXAMPLE 9

(S)-1-[6-Amino-2-[(hexylhydroxyphosphinyl)oxy]-1-oxohexyl]-L-proline (a)

Hexylphosphinic acid, 1-adamantanamine salt

Concentrated sulfuric acid (15 ml.) is added to a suspension of sodium hypophosphite hydrate (60 g., 566 mmole, 3.0 eq.) in absolute ethanol (600 ml.) followed by 1-hexene (15.9 g., 189 mmole, 1 eq.). The mixture is treated with 2,2'-azobisisobutyronitrile (2.0 g.), refluxed for 4 hours, treated again with 2,2'-azobisisobutyronitrile (2.0 g.) and refluxed for an additional 16 hours. The cooled mixture is filtered, the filtrate evaporated, suspended in water (200 ml.) and made basic with 50% sodium hydroxide solution (approximately 25 ml.), and then washed with ethyl ether (2×200 ml.). The aqueous phase is acidified with concentrated sulfuric acid (12 ml.) and extracted with ethyl acetate. The organic phase is washed with brine, dried over anhydrous sodium sulfate, and evaporated to give 24.82 g. of crude hexylphosphinic acid as a colorless viscous oil.

This crude acid (15 g., 100 mmole) is taken up in ethyl acetate (200 ml.) and treated with a solution of 1-adamantanamine (15.1 g, 100 mmole) in ethyl acetate (200 ml.). The precipitated salt is collected by filtration and dried in vacuo to give 27.77 g. of hexylphosphinic acid, 1-adamantanamine salt. TLC (silica gel; isopropanol:ammonia:water, 7:21) $R_f = 0.64$.

(b)

1-[(S)-6-[[(Phenylmethoxy)carbonyl]amino]-2-[(hexylphosphinyl)oxy]-1-oxohexyl]-L-proline, phenylmethyl ester The 1-adamantanamine salt product from part (a) (1.45 g., 4.82 mmole, 1.5 eq.) is dissolved in 1.0N hydrochloric acid and extracted with ethyl acetate. The organic phase is washed with brine, dried over anhydrous sodium sulfate, and evaporated to give hexylphosphinic acid as a clear oil. This oil is dissolved in dry tetrahydrofuran (20 ml.), 1-[(S)-6-[[(phenylmethoxy)carbonyl]amino]-2-hydroxy-1-oxohexyl]-L-proline, phenylmethyl ester (1.5 g., 3.21 mmole, 1 eq.), dicyclohexylcarbodiimide (995 mg., 4.82 mmole, 1.5 eq.), and dimethylaminopyridine (59 mg., 0.15 eq.) are added. The white suspension is stirred for 5 hours under argon at room temperature. The mixture is diluted with ethyl acetate, precipitated dicyclohexyl urea is removed by filtration, and the filtrate is washed with 5% potassium bisulfate, saturated sodium bicarbonate, and brine, then dried over anhydrous sodium sulfate, and evaporated to an oil. The crude oil is taken up in ethyl acetate (5 ml.) and chromatographed on a pad of silica gel (SiliCAR CC-7) eluting with ethyl ether:acetone (3:2). Product fractions are pooled and evaporated, taken up in ethyl acetate, filtered again, and evaporated to give 2.145 g. of 1-[(S)-6-[[(phenylmethoxy)carbonyl]amino]-2-[(hexylphosphinyl)oxy]-1-oxohexyl]-L-proline, phenylmethyl ester as an oily semi-solid. TLC (silica gel; ethyl ether:acetone, 8:2) $R_f = 0.20$.

(c)

1-[(S)-6-[[(Phenylmethoxy)carbonyl]amino]-2-[(hexylhydroxyphosphinyl)oxy]-1-oxohexyl]-L-proline, phenylmethyl ester, 1-adamantanamine salt A mixture of the phenylmethyl ester product from part (b) (2.145 g., 3.57 mmole) in dioxane (12 ml.) is treated with an aqueous solution of sodium periodate (791 mg., 3.7 mmole, 1.15 eq. in 4 ml. of water). The white suspension is stirred overnight under argon at room temperature. The orange suspension is partitioned between 1% potassium bisulfate and ethyl acetate. The organic layer is washed with water, dilute sodium bisulfite (enough to discharge color), and brine, then dried over anhydrous sodium sulfate, and evaporated to an oil. The residue is taken up in ethyl acetate, residual dicyclohexyl urea is filtered off, and the mixture is evaporated. Purification of the crude oil is accomplished by dissolving the oil in ethyl acetate (4 ml.) and ethyl ether (10 ml.) and treating it with an ethereal solution of 1-adamantanamine (600 mg. in 5 ml. of ethyl ether). The precipitated solid is filtered under a blanket of argon and then dried in vacuo to give 2.205 g. of 1-[(S)-6-[[(phenylmethoxy)carbonyl]amino]-2-[(hexylhydroxyphosphinyl)oxy]-1-oxohexyl]-L-proline, 1-adamantanamine salt as an off-white solid; m.p. 133°–136°. TLC (silica gel; methylene chloride:methanol:acetic acid, 20:1:1) $R_f = 0.27$.

(d)

(S)-1-[6-Amino-2-[(hexylhydroxyphosphinyl)oxy]-1-oxohexyl]-L-proline

The 1-adamantanamine salt product from part (c) (2.205 g.) is dissolved in 1.0N hydrochloric acid (50 ml.), extracted with ethyl acetate, the organic layer is washed with brine, dried over anhydrous sodium sulfate, and evaporated to give 1-[(S)-6-[[(phenylmethoxy)carbonyl]amino]-2-[(hexylhydroxyphosphinyl)oxy]-1-oxohexyl]-L-proline, phenylmethyl ester as a clear oil. This oil is dissolved in methanol (10 ml.), the solution is purged with bubbling argon, and then 10% palladium on carbon catalyst (265 mg., 15% by weight) is added. The black suspension is stirred under hydrogen for one hour. The catalyst is removed by filtration through dry, packed Celite, and the filtrate is evaporated. The solid white residue is taken up in water (50 ml.), filtered through a polycarbonate membrane, evaporated, and azeotroped once with acetonitrile to give 1.003 g. of (S)-1-[6-amino-2-[(hexylhydroxyphosphinyl)oxy]-1-oxohexyl]-L-proline as a white granular solid; m.p. 160°–170° (with yellowing); $[\alpha]_D^{22} = -49°$ (c=0.5, methanol). TLC (silica gel; isopropanol:ammonia:water, 7:2:1) $R_f$=0.26.

Anal. Calc'd for $C_{17}H_{33}N_2O_6P \cdot 1.0H_2O$: C, 49.75; H, 8.60; N, 6.83; P, 7.55. Found: C, 49.79; H, 8.44; N, 6.72; P, 7.20.

EXAMPLE 10

1-[(S)-6-Amino-2-[(heptylhydroxyphosphinyl)oxy]-1-oxohexyl]-L-proline (a)

Heptylphosphinic acid, 1-adamantanamine salt

Sodium hypophosphite (22.5 g., 212 mmole) is added to a solution of 1-heptene (6.6 g., 67.2 mmole) in absolute ethanol (225 ml.), followed by the addition of concentrated sulfuric acid (5.6 ml.). This mixture is treated with 2,2'-azobisisobutyronitrile (1.1 g.), refluxed for 5 hours, treated again with 2,2'-azobisisobutyronitrile (0.7 g.), and refluxed overnight. The reaction mixture is cooled, filtered, and the filtrate is concentrated in vacuo. The concentrate is diluted with water (70 ml.), made basic with 50% sodium hydroxide, and washed with ethyl ether (2×100 ml.). The aqueous phase is acidified with concentrated sulfuric acid, and the product is extracted with ethyl acetate. The organic phase is washed with saturated sodium chloride solution, dried over sodium sulfate, and concentrated in vacuo to yield 11.9 g. of crude heptylphosphinic acid as a viscous oil. A solution of this crude acid in ethyl acetate (70 ml.) is treated with 1-adamantanamine (10.6 g.) in 100 ml. of ethyl acetate. The precipitated salt is filtered and dried in vacuo to yield 18.5 g. of heptylphosphinic acid, 1-adamantanamine salt.

(b)

1-[(S)-6-[[(Phenylmethoxy)carbonyl]amino]-2-[(heptylphosphinyl)oxy]-1-oxohexyl]-L-proline, phenylmethyl ester The 1-adamantanamine salt from part (a) (3.15 g., 10 mmole) is dissolved in 1N hydrochloric acid and extracted with ethyl acetate. The organic phase is washed with brine, dried over anhydrous sodium sulfate, and concentrated in vacuo to yield 1.7 g. of heptylphosphinic acid. This acid is dissolved in dry tetrahydrofuran (20 ml.) along with 1-[(S)-6-[[(phenylmethoxy)carbonyl]amino]-2-hydroxy-1-oxohexyl]-L-proline, phenylmethyl ester (3.12 g., 6.66 mmole) and cooled to 0°. Dicyclohexylcarbodiimide (2.06 g., 10 mmole) and dimethylaminopyridine (0.12 g.) are added and the reaction mixture is stirred under argon at 0° for 5 hours then at room temperature overnight. The mixture is diluted with ethyl acetate (120 ml.), filtered, and the filtrate washed with 5% potassium bisulfate, saturated sodium bicarbonate, and brine, then dried over anhydrous sodium sulfate, and concentrated in vacuo. The resulting oil is dissolved in ethyl acetate (5 ml.), layered over a pad of silica gel (¾ inch pad of SiliCAR CC-7), and eluted with ethyl ether:acetone (8:2) by filtration. The filtrate is concentrated in vacuo to yield 3.95 g. of crude 1-[(S)-6-[[(phenylmethoxy)carbonyl]amino]-2-[(heptylphosphinyl)oxy]-1-oxohexyl]-L-proline, phenylmethyl ester. TLC (silica gel; ethyl ether:acetone, 8:2) $R_f$=0.15.

(c)

1-[(S)-6-[[(Phenylmethoxy)carbonyl]amino]-2-[(heptylhydroxyphosphinyl)oxy]-1-oxohexyl]-L-proline, phenylmethyl ester The phenylmethyl ester product from part (b) (3.95 g., 6.2 mmole) in dioxane (20 ml.) is treated with an aqueous solution of sodium periodate (1.7 g., 8.0 mmole in 10 ml. of water). The white suspension is stirred under argon overnight at room temperature. The reaction mixture is diluted with ethyl acetate (150 ml.) and the organic phase is washed with 1% potassium bisulfate (2×50 ml.), water and brine (2×50 ml.), dried over sodium sulfate, and concentrated in vacuo to yield 3.7 g. of crude 1-[(S)-6-[[(phenylmethoxy)carbonyl]aino]-2-[(heptylhydroxyphosphinyl)oxy]-1-oxohexyl]-L-proline, phenylmethyl ester.

1-Adamantanamine (1.0 g.) in ethyl ether (10 ml.) is added to a solution of this crude phenylmethyl ester product in ethyl acetate-ethyl ether (1:25). The precipitated solid is filtered and dried to yield 3.0 g. of the 1-adamantanamine salt product. This salt product is partitioned between ethyl acetate (100 ml.) and 1N hydrochloric acid (50 ml.). The organic phase is washed with water and brine, dried over anhydrous sodium sulfate, and concentrated in vacuo to yield 2.1 g. of purified 1-[(S)-6-[[(phenylmethoxy)carbonyl]amino]-2-[(heptylhydroxyphosphinyl)oxy]-1-oxohexyl]-L-proline, phenylmethyl ester.

(d)

1-[(S)-6-Amino-2-[(heptylhydroxyphosphinyl)oxy]-1-oxohexyl]-L-proline

The phenylmethyl ester product from part (c) (2.1 g.) is hydrogenated for one hour in methanol (20 ml.) using 20% palladium hydroxide carbon catalyst. The catalyst is removed by filtration through Celite and the filtrate is concentrated in vacuo. The resulting oil is dissolved in water (30 ml.) and this solution is filtered through a polycarbonate membrane. The filtrate is evaporated to 20 ml. and the crystallized product is filtered and dried in vacuo to give 0.7 g. of 1-[(S)-6-amino-2-[(heptylhydroxyphosphinyl)oxy]-1-oxohexyl]-L-proline; m.p. 180°–186° (decomposition at 190°); $[\alpha]_D^{22} = -54.4°$ (c=0.5, methanol) TLC (silica gel; isopropanol:ammonia:water, 7:2:1) $R_f$=0.23.

Anal. calc'd for $C_{21}H_{35}N_2PO_6 \cdot 0.8H_2O$: C, 51.37; H, 8.77; N, 6.66; P, 7.36. Found: C, 51.43; H, 8.45; N, 6.57; P, 7.10.

EXAMPLE 11

(S)-1-[6-Amino-2-[(hydroxyoctylphosphinyl)oxy]-1-oxohexyl]-L-proline (a)

Octylphosphinic acid, 1-adamantanamine salt

Concentrated sulfuric acid (15 ml.) is added to a suspension of sodium hypophosphite hydrate (60 g.) and 1-octene (21.2 g.) in absolute ethanol and the mixture is treated with 2,2'-azobisisobutyronitrile (3.0 g.). The suspension is refluxed for 3 hours, additional 2,2'-azobisisobutyronitrile (2.0 g.) is added and the mixture is refluxed for 16 more hours. The cooled mixture is filtered, the filtrate evaporated, suspended in water (200 ml.), made basic with 50% sodium hydroxide (approximately 25 ml., pH 13), and washed with ethyl ether (2×200 ml.). The aqueous phase is acidified with concentrated sulfuric acid and extracted with ethyl acetate. The organic phase is washed with brine, dried over anhydrous sodium sulfate and evaporated to give 28.86 g. of crude octylphosphinic acid as a colorless, viscous oil.

This crude acid (17.8 g.) is dissolved in ethyl acetate (200 ml.) and treated with an ethyl acetate solution of 1-adamantanamine (15.1 g. in 200 ml. of ethyl acetate). The precipitated salt is collected by filtration, washed with ethyl acetate, and dried in vacuo to give 29.5 g. of octylphosphinic acid, 1-adamantanamine salt as a white solid. TLC (silica gel; isopropanol:ammonia:water, 7:2:1) $R_f=0.63$.

(b)

1-[(S)-6-[[(Phenylmethoxy)carbonyl]amino]-2-[(octylphosphinyl)oxy]-1-oxohexyl]-L-proline, phenylmethyl ester The 1-adamantanamine salt product from part (a) is partitioned between 1.0N hydrochloric acid and ethyl acetate. The organic phase is washed with brine, dried over anhydrous sodium sulfate, and evaporated to a clear oil. A mixture of this acid (857 mg., 2.60 mmole, 1.5 eq.) and 1-[(S)-6-[[(phenylmethoxy)carbonyl]amino]-2-hydroxy-1-oxohexyl]-L-proline, phenylmethyl ester (811 mg., 1.73 mmole, 1.0 eq.) in dry tetrahydrofuran (15 ml.) is treated with dicyclohexylcarbodiimide (536 mg., 2.6 mmole, 1.5 eq.) and dimethylaminopyridine (180 mg., 0.51 eq.). The resulting white suspension is stirred overnight under argon. The mixture is diluted with ethyl acetate, dicyclohexyl urea is filtered off, and the filtrate is washed with 5% potassium bisulfate, saturated sodium bicarbonate, and brine, then dried over anhydrous sodium sulfate, and evaporated. The residue is taken up in ethyl acetate and chromatographed on a ¾ inch pad of silica gel (SiliCAR CC-7) eluting with ethyl ether:acetone (3:2). The product containing fractions are combined, evaporated, taken up in ethyl acetate, residual dicyclohexyl urea is filtered off, and the filtrate is evaporated to give 1-[(S)-6-[[(phenylmethoxy)carbonyl]amino]-2-[(octylphosphinyl)oxy]-1-oxohexyl]-L-proline, phenylmethyl ester as a clear oil. TLC (silica gel; ethyl ether:acetone, 8:2) $R_f=0.18$.

(c)

1-[(S)-6-[[(Phenylmethoxy)carbonyl]amino]-2-[(hydroxyoctylphosphinyl)oxy]-1-oxohexyl]-L-proline, phenylmethyl ester, 1-adamantanamine salt A mixture of the phenylmethyl ester product from part (b) (909 mg., 1.45 mmole) in dioxane (10 ml.) is treated with an aqueous sodium periodate solution (357 mg., 1.15 eq. in 4 ml. of water) and the mixture is stirred overnight under argon at room temperature. The orange suspension is partitioned between ethyl acetate and 1% potassium bisulfate. The organic phase is washed with water, dilute sodium bisulfite, and brine, then dried over anhydrous sodium sulfate, and evaporated to an oil. This crude oil is purified by dissolving it in ethyl acetate (2 ml.) and ethyl ether (10 ml.) and treating with an ethereal solution of 1-adamantanamine (260 mg., 1.7 mmole in 10 ml. of ethyl ether). The precipitated salt is collected by filtration under a blanket of argon and then dried in vacuo to give 875 mg. of 1-[(S)-6-[[(phenylmethoxy)carbonyl]amino]-2-[(hydroxyoctylphosphinyl)oxy]-1-oxohexyl]-L-proline, phenylmethyl ester, 1-adamantanamine salt as a white solid. TLC (silica gel; methylene chloride:methanol:acetic acid, 20:1:1) $R_f=0.57$.

(d)

(S)-1-[6-Amino-2-[(hydroxyoctylphosphinyl)oxy]-1-oxohexyl]-L-proline

The 1-adamantanamine salt product from part (c) is partitioned between 1.0N hydrochloric acid and ethyl acetate. The organic phase is washed with brine, dried over anhydrous sodium sulfate, and evaporated to give 709 mg. of 1-[(S)-6-[[(phenylmethoxy)carbonyl]amino]-2-[(hydroxyoctylphosphinyl)oxy]-1-oxohexyl]-L-proline, phenylmethyl ester as a clear oil.

An argon purged solution of this oil (709 mg.) in methanol (11 ml.) is treated with 10% palladium on carbon catalyst (106 mg., 15% by weight). The black suspension is stirred under hydrogen for 1.5 hours. The catalyst is removed by filtration through dry, packed Celite, the filtrate is evaporated, taken back up in water (50 ml.), filtered through a polycarbonate membrane, and evaporated. The residue is azetroped once with acetonitrile and then dried in vacuo to give 398 mg. of (S)-1-[6-amino-2-[(hydroxyoctylphosphinyl)oxy]-1-oxohexyl]-L-proline as a hydrated white solid; m.p. 168°-172° (decomposition); $[\alpha]_D^{22}=-48°$ (c=0.5, methanol). TLC (silica gel; isopropanol:ammonia:water, 7:2:1) $R_f=0.22$.

Anal. calc'd. for $C_{19}H_{37}N_2O_6P.1.5H_2O$: C, 50.99; H, 9.01; N, 6.26; P, 6.92. Found: C, 50.99; H, 8.62; N, 6.25; P, 6.70.

EXAMPLE 12

(S)-1-[6-Amino-2-[(octylhydroxyphosphinyl)oxy]-1-oxyhexyl]-L-proline, dilithium salt (a)

Octylphosphonic acid, dibenzyl ester

A suspension of prewashed (hexane) sodium hydride (1.43 g., 57 mmole, 1.1 eq.) in dry dimethylformamide (45 ml.) is treated dropwise with dibenzylphosphite (11.5 ml., 52 mmole, 1 eq.) and the mixture is stirred at room temperature for 2 hours. n-Octyl bromide (8.95 ml., 52 mmole, 1 eq.) is added and the resulting suspension (sodium bromide precipitate is noticed) is stirred for 3.5 hours under argon at room temperature. The mixture is partitioned between 5% potassium bisulfate and ethyl acetate. The organic phase is washed with brine, dried over anhydrous sodium sulfate, and evaporated to a yellow oil (16.88 g.). The crude oil is purified by flash chromatography on silica gel (LPS-1) eluting with hexane:ethyl acetate (3:1). Evaporation of the product containing fractions gives 8.51 g. of octylphosphonic acid, dibenzyl ester as a clear oil. TLC (silica gel; hexane:ethyl acetate, 8:2) $R_f=0.14$.

(b)

1-[(S)-2-[[(Octyl)(phenylmethoxy)phosphinyl]oxy]-6-[[(phenylmethoxy)carbonyl]amino]-1-oxohexyl]-L-proline, phenylmethyl ester A mixture of octylphosphonic acid, dibenzyl ester (644 mg., 1.72 mmole, 1.5 eq.) in dry benzene (10 ml.) is treated with phosphorus pentachloride (379 mg., 1.82 mmole, 1.7 eq.) and the mixture is stirred under argon at 75° (oil bath) for 3 hours. The mixture is evaporated to dryness (0.5 mm. of Hg.), taken up in benzene (10 ml.), evaporated, and this procedure is repeated twice more. The residue is taken up in dry methylene chloride (10 ml.), 1-[(S)-6-[[(phenylmethoxy)carbonyl]amino]-2-hydroxy-1-oxohexyl]-L-proline, phenylmethyl ester (500 mg., 1.07 mmole, 1 eq.) is added, the solution is cooled to 0° (ice-bath), treated with triethylamine (0.24 ml., 1.72 mmole, 1.5 eq.) and dimethylaminopyridine (21 mg., 0.15 eq.), then stirred at 0° for 30 minutes and at room temperature for 1.5 hours. The mixture is partitioned between methylene chloride and 5% potassium bisulfate, the organic phase is washed with brine, dried over anhydrous sodium sulfate, and evaporated to a light brown oil (865 mg.). The crude oil is purified by flash chromatography on silica gel (LPS-1) eluting with hexane:acetone (7:3). The product containing fractions are combined and evaporated and the remaining polar impurities are removed by filtration through neutral alumina (Act III) eluting with hexane:acetone (7:3). The product containing fractions are combined and evaporated to give 282 mg. of 1-[(S)-2-[[(octyl)(phenylmethoxy)phosphinyl]oxy]-6-[[(phenylmethoxy)carbonyl]amino]-1-oxohexyl]-L-proline, phenylmethyl ester as a clear, colorless oil. TLC (silica gel; methylene chloride:acetone, 4:1) $R_f=0.53$.

(c)

(S)-1-[6-Amino-2-[(octylhydroxyphosphinyl)oxy]-1-oxohexyl]-L-proline, dilithium salt 10% Palladium on carbon catalyst (56 mg., 20% by weight) is added to an argon purged solution of the phenylmethyl ester product from part (b) (280 mg., 0.387 mmole) in methanol (6 ml.), water (0.5 ml.), and triethylamine (0.16 ml., 1.16 mmole, 3 eq.). The black suspension is stirred under hydrogen for one hour. The catalyst is removed by successive filtration through dry packed Celite and then a polycarbonate filter and prefilter. The filtrate is evaporated to a white foam, taken up in 1.0N lithium hydroxide (3 ml.), and chromatographed (HP-20 resin) eluting with water→acetonitrile gradient system. The product containing fractions are combined and evaporated to give 100 mg. of fluffy, white (S)-1-[6-amino-2-[(octylhydroxyphosphinyl)oxy]-1-oxohexyl]-L-proline, dilithium salt; m.p. softens at 190°, 205°–209°; $[\alpha]^{22}=-43.6°$ (c=0.5, methanol). TLC (silica gel, isopropanol:ammonia:water, 7:2:1) $R_f=0.26$.

Anal. calc'd. for $C_{19}H_{35}N_2O_6P.2Li.2.3H_2O$: C, 48.16; H, 8.42; N, 5.91; P, 6.54. Found: C, 48.11; H, 8.06; N, 5.65; P, 6.50.

EXAMPLE 13

(S)-1-[2-[[Hydroxy(4-phenylbutyl)phosphinyl]oxy]-1-oxopropyl]-L-proline, dilithium salt (a)

1-[(S)-2-[[(4-Phenylbutyl)(phenylmethoxy)phosphinyl]oxy]-1-oxopropyl]-L-proline, phenylmethyl ester A stirred solution of (4-phenylbutyl)phosphonic acid, dibenzyl ester (1.5 g., 3.58 mmole) in dry benzene (10 ml.) is treated with phosphorus pentachloride (820 mg., 3.94 mmole, 1.1 eq.) and heated under argon at 75° (oil bath) for 3 hours. The mixture is evaporated (0.5 mm. of Hg.), taken up in benzene (8 ml.), evaporated again and this procedure is repeated twice more. The residue is taken up in dry methylene chloride (10 ml.), cooled to 0° (ice bath) and treated with 1-[(S)-2-hydroxyl-1-oxopropyl]-L-proline, phenylmethyl ester [prepared as set forth in Example 2(c) of U.S. Pat. No. 4,452,790] (646 mg., 2.33 mmole, 0.65 eq.), triethylamine (0.502 ml., 3.58 mmole, 1 eq.), and dimethylaminopyridine 44 mg., 0.358 mmole, 0.1 eq.). After 2 hours stirring at room temperature, the mixture is partitioned between 5% potassium bisulfate and ethyl acetate. The organic layer is washed with brine, dried over anhydrous sodium sulfate, and evapoated to a yellow oil. The crude oil is flash chromatographed on silica gel (LPS-1) eluting with hexane:acetone (7.3). Product containing fractions are combined and evaporated to give 869 mg. of 1-[(S)-2-[[(4-phenylbutyl)(phenylmethoxy)phosphinyl]oxy]-1-oxopropyl]-L-proline, phenylmethyl ester as a clear oil. TLC (silica gel; methylene chloride:methanol, 9:1) $R_f=0.51$.

(b)

(S)-1-[2-[[Hydroxy(4-phenylbutyl)phosphinyl]oxy]-1-oxopropyl]-L-proline, dilithium salt 10% Palladium on carbon catalyst (129 mg., 15% by weight) is added to an argon purged solution of the phenylmethyl ester product from part (a) (860 mg., 1.53 mmole) in methanol (10 ml.), water (2 ml.), and triethylamine (641 ml., 4.6 mmole, 3 eq.) and the suspension is stirred for one hour under hydrogen. The mixture is filtered through Celite, evaporated, taken up in water (5 ml.), filtered through a polycarbonate filter and prefilter, and then chromatographed on AG-50 W-X8 Li+ form resin. Product containing fractions are combined and lyophilized to give 552 mg. of white, granular (S)-1-[2-[[hydroxy(4-phenylbutyl)phosphinyl]oxy]-1-oxopropyl]-L-proline, dilithium salt; $[\alpha]_D^{22}=-58.6°$ (c=0.5, methanol). TLC (silica gel; isopropanol:ammonia:water; 7:2:1) $R_f=0.48$.

Anal calc'd. for $C_{18}H_{24}NO_6P.2Li.2.5H_2O$: C, 49.10; H, 6.64; N, 3.18; P, 7.03. Found: C, 49.17; H, 6.39; N, 3.18; P, 6.70.

EXAMPLE 14

(S)-1-[2-[(Hexylhydroxyphosphinyl)oxy]-1-oxopropyl]-L-proline, dilithium salt (a)

1-[(S)-2-[[(Phenylmethoxy)hexylphosphinyl]oxy]-1-oxopropyl]-L-proline, phenylmethyl ester A solution of hexylphosphonic acid, dibenzyl ester (1.5 g., 4.33 mmole, 1.5 eq.) in dry benzene (10 ml.) is treated with phosphorus pentachloride (992 mg., 4.76 mmole, 1.65 eq.) and the mixture is stirred and heated at 70° (oil bath) under argon for two hours. The mixture is evaporated to dryness (0.5 mm of Hg.), the residue is taken up in benzene (8 ml.), evaporated again and this procedure is repeated twice more. The residue is dissolved in dry methylene chloride (10 ml.), cooled to 0° (ice bath), and treated with 1-[(S)-2-hydroxy-1-oxopropyl]-L-proline, phenylmethyl ester (801 mg., 2.89 mmole, 1 eq.), triethylamine (604 ml., 4.33 mmole, 1.5 eq.) and dimethylaminopyridine (53 mg., 0.433 mmole, 1 eq.). After one hour at 0° and one hour at room temperature, the mixture is partitioned between 5% potassium bisulfate and ethyl acetate. The organic phase is washed with brine, dried over anhydrous sodium sulfate, and evaporated to a yellow oil. This crude oil is chromatographed on silica gel (LPS-1) eluting with hexane:acetone (8:2). The product containing fractions are combined and evaporated to give 735 mg. of 1-[(S)-

2-[[(phenylmethoxy)hexylphosphinyl]oxy]-1-oxopropyl]-L-proline, phenylmethyl ester as a clear light yellow oil. TLC (silica gel; methylene chloride:acetone) $R_f=0.63$.

(b)

(S)-1-[2-[(Hexylhydroxyphosphinyl)oxy]-1-oxopropyl]-L-proline, dilithium salt

10% Palladium on carbon catalyst (110 mg., 15% by weight) is added to an argon purged solution of the phenylmethyl ester product from part (a) (735 mg., 1.35 mmole) in methanol (10 ml.), water (2 ml.), and triethylamine (0.565 ml., 4.05 mmole, 3 eq.) and the suspension is stirred under hydrogen for 1.5 hours. The mixture is filtered through a Celite bed, evaporated, taken up in water, filtered through a polycarbonate filter and prefilter, and then chromatographed on an AG-50W-X8 Li+ form resin eluting with water. Product containing franctions are lyophilized to give 442 mg. of (S)-1-[2-[(hexylhydroxyphosphinyl)oxy]-1-oxopropyl]-L-proline, dilithium salt as a white granular solid; $[\alpha]_D^{22}=-63.2°$ (c=0.5, methanol). TLC (silica gel; isopropanol:ammonia:water, 7:2:1) $R_f=0.56$.

Anal. calc'd. for $C_{14}H_{24}NO_6P \cdot 2Li \cdot 1.6H_2O$: C, 44.72; H, 7.29; N, 3.72; P, 8.24. Found: C, 44.74; H, 7.25; N, 3.66; P, 7.90.

EXAMPLE 15

(S)-1-[2-[[[1-(Benzoylamino)pentyl]hydroxyphosphinyl]oxy]-1-oxopropyl]-L-proline, dilithium salt (a) 1-[(Diphenyl)methylamino]pentylphosphinic acid A solution of 50% aqueous hypophosphorous acid (55 g., 0.296 mole) in dioxane (100 ml.) is added all at once to a solution of aminodiphenylmethane (0.296 mole) in dioxane (100 ml.) with vigorous stirring. The salt crystallizes within minutes from the resulting warm solution. After refrigeration, the product is recovered by filtration to give 65.7 g. of aminodiphenylmethane, hypophosphorous acid salt; m.p. 171°–173°.

Anal. calc'd for $C_{13}H_{16}NO_2P$: C, 62.64; H, 6.47; N, 5.62; P, 12.40. Found: C, 62.63; H, 6.52; N, 5.55; P, 12.20.

A mixture of aminodiphenylmethane, hypophosphorous acid (6.25, 0.024 mole) and valeraldehyde (20 ml., 0.19 mole freshly distilled) is warmed at 65°–70° for 15 minutes. The resulting semi-solid mass is diluted to a volume of 75 ml. with ethanol. The solid that separates from the solution is collected by filtration and washed with ether to give 3.8 g. of 1-[(diphenyl)methylamino]pentylphosphinic acid; m.p. 203°–205° (turbid melt).

(b)

1-(Amino)pentylphosphinic acid

A mixture of 1-[(diphenyl)methylamino]pentylphosphinic acid (5 g., 15 mmole), anisole (5 ml.) and trifluoroacetic acid (50 ml.) is refluxed for one hour under argon. It is then partitioned between water (100 ml.) and ether (100 ml.). The aqueous layer is filtered and concentrated in vacuo, chasing traces of solvent with ethanol. This gives a white solid which is triturated with acetonitrile and dried overnight in vacuo to give 1.49 g. of 1-(amino)pentylphosphinic acid.

(c)

1-[[(Phenylmethoxy)carbonyl]amino]pentylphosphinic acid

The pH of a solution of 1-(amino)pentylphosphinic acid (1.95 g., 12.9 mmole in 50 ml. of water) is adjusted to 9.5 by the addition of 2.5N sodium hydroxide. After cooling the solution to 0°, benzyl chloroformate (1.95 ml., 2.2 g., 12.9 mmole) is added in small portions, with additional sodium hydroxide to maintain a pH of 9.5. The mixture is stirred for 2 hours at 0° at this pH. The reaction mixture is extracted with ether to remove unreacted benzyl chloroformate. The reaction mixture is then acidified with concentrated hydrochloric acid to pH 2, and then extracted with ethyl acetate. The combined ethyl acetate extracts are dried over sodium sulfate and concentrated in vacuo to give 2.93 g. of 1-[[(phenylmethoxy)carbonyl]amino]pentylphosphinic acid.

(d)

(S)-1-[2-[[[1-[[(Phenylmethoxy)carbonyl]amino]pentyl]hydroxyphosphinyl]oxy]-1-oxopropyl]-L-proline, phenylmethyl ester A solution of 1-[[(phenylmethoxy)carbonyl]amino]pentylphosphinic acid (490 mg., 1.72 mmole) and 1-[(S)-2-hydroxy-1-oxopropyl]-L-proline, phenylmethyl ester (255 mg., 0.92 mmole) in dry tetrahydrofuran (5 ml.) is treated with dicyclohexylcarbodiimide (285 mg., 1.38 mmole) and dimethylaminopyridine (50 mg.) and stirred at room temperature for 2.5 hours. The mixture is filtered, diluted with ethyl acetate, and washed successively with 5% potassium bisulfate, saturated sodium bicarbonate, and saturated sodium chloride solutions, dried over sodium sulfate, and evaporated to give crude (S)-1-[2-[[[1-[[(phenylmethoxy)carbonyl]amino]pentyl]phosphinyl]oxy]-1-oxopropyl]-L-proline, phenylmethyl ester.

This crude phenylmethyl ester material is taken up in dioxane (5 ml.), treated with a solution of sodium periodate (250 mg., 1.17 mmole) in water (3 ml.) and stirred overnight at room temperature. The mixture is partitioned between ethyl acetate and 1% potassium bisulfate. The organic phase is washed with dilute sodium bisulfate and saturated sodium chloride, dried over sodium sulfate, and evaporated. This crude product is taken up in ether (about 10 ml.) and treated with a solution of 1-adamantanamine (150 mg., 1.0 mmole) in hexane (5 ml.). The solution is evaporated to dryness and the residue is triturated with hexane to give 563 mg. of (S)-1-[2-[[[1-[[(phenylmethoxy)carbonyl]amino]pentyl]hydroxyphosphinyl]oxy]-1-oxopropyl]-L-proline, phenylmethyl ester, 1-adamantanamine salt.

This salt is partitioned between ethyl acetate and 1N hydrochloric acid. The ethyl acetate phase is washed with 1N hydrochloric acid and saturated sodium chloride solutions, dried over sodium sulfate, and evaporated to give 435 mg. of (S)-1-[2-[[[1-[[(phenylmethoxy)carbonyl]amino]pentyl]hydroxyphosphinyl]oxy]-1-oxopropyl]-L-proline, phenylmethyl ester as a colorless glass. TLC (silica gel; methylene chloride:acetic acid:methanol, 20:1:1) $R_f=0.12$.

(e)

(S)-1-[2-[[[1-(Amino)pentyl]hydroxyphosphinyl]oxy]-1-oxopropyl]-L-proline

The phenylmethyl ester product from part (d) (1.8 g., 3.2 mmole) is dissolved in methanol (50 ml.) and 10% palladium hydroxide on carbon catalyst (280 mg.) is added. The mixture is stirred under atmospheric hydrogen for 6 hours. The methanol solution is filtered through Celite and concentrated in vacuo to give 780 mg. of white solid (S)-1-[2-[[[1-(amino)pentyl]hydroxyphosphinyl]oxy]-1-oxopropyl]-L-proline. TLC (silica gel; isopropanol:ammonia:water, 7:2:1) $R_f$=0.53.

(f)

(S)-1-[2-[[[1-(Benzoylamino)pentyl]hydroxyphosphinyl]oxy]-1-oxopropyl]-L-proline, dilithium salt A suspension of the product from part (d) (0.33 g., 1.0 mmole) in dry acetonitrile (10 ml.) is treated with bistrifluoromethylsilylacetamide (0.93 ml., 3.50 mmole) and stirred at room temperature under argon for 1.5 hours. The resulting clear solution is treated with benzoyl chloride (0.13 ml., 1.12 mmole) and stirred at room temperature under argon for 1 hour. The mixture is evaporated to dryness, taken up in acetonitrile (10 ml.)-water (4 ml.) and stirred at room temperature for 15 minutes. The mixture is then evaporated to dryness and azeotroped with acetonitrile to remove the residual water. The residue is triturated with ether to give crude (S)-1-[2-[[[1-(benzoylamino)pentyl]hydroxyphosphinyl]oxy]-1-oxopropyl]-L-proline as a white solid.

This crude product is taken up in 1N lithium hydroxide (2.5 ml., 2.5 mmole) and chromatographed on an HP-20 column eluting with a water-acetonitrile gradient. The product containing fractions are combined and evaporated. The glassy residue is taken up in water, filtered (millipore) and lyophilized to give (S)-1-[2-[[[1-(benzoylamino)pentyl]hydroxyphosphinyl]oxy]-1-oxopropyl]-L-proline, dilithium salt as a white granular solid; $[\alpha]^{22}$=-48.8° (c=0.5, methanol). TLC (silica gel; methylene chloride:acetic acid:methanol, 8:1:1) $R_f$=0.29.

Anal. calc'd for $C_{20}H_{27}N_2O_7 \cdot 2Li \cdot 1.55H_2O$: C, 50.02; H, 6.32; N, 5.83; P, 6.45. Found: C, 50.02; H, 6.39; N, 5.87; P, 6.10.

EXAMPLE 16

1000 Tablets each containing the following ingredients

| | |
|---|---|
| (S)—1-[6-Amino-2-[[hydroxy(4-phenylbutyl)phosphinyl]oxy]-1-oxohexyl]-L-proline | 100 mg. |
| Cornstarch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S)-1-[6-amino-2-[[hydroxy(4-phenylbutyl)phosphinyl]oxy]-1-oxohexyl]-L-proline and cornstarch with an aqueous solution of the gelatin. The mixture is dried and ground to a fine powder. The Avicel and then the magnesium stearate are admixed with granulation. The mixture is compressed in a tablet press to form 1000 tablets each containing 100 mg. of active ingredient.

In a similar manner, tablets containing 100 mg. of the product of any Examples 1 to 3 and 5 to 12 can be prepared.

EXAMPLE 17

1000 Tablets each containing the following ingredients

| | |
|---|---|
| (S)—1-[6-Amino-2-[[hydroxy(4-phenylbutyl)phosphinyl]oxy]-1-oxohexyl]-L-proline | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (S)-1-[6-amino-2-[[hydroxy(4-phenylbutyl)phosphinyl]oxy]-1-oxohexyl]-L-proline, Avicel, and a portion of the stearic acid. The slugs are ground and passed through a #2 screen and then mixed with the hydrochlorothiazide, lactose, cornstarch, and the remainder of stearic acid. The mixture is compressed into 350 mg. capsule shaped tablets in a tablet press. The tablets are scored for dividing in half.

In a similar manner, tablets can be prepared containing 100 mg. of the product of any of Examples 1 to 3 and 5 to 12.

EXAMPLE 18

The compounds of formula I were tested in vivo in conscious, normotensive rats. Angiotensin I given intravenously increases blood pressure due to conversion to angiotensin II via the angiotensin converting enzyme (ACE). ACE inhibition was reflected by the attenuation of an angiotensin I pressor response after compound administration. The in vivo testing procedure is described in greater detail by Rubin et al., "SQ14,225 (D-3-Mercapto-2-Methylpropanoyl-L-Proline), A Novel Orally Active Inhibitor Of Angiotensin I Converting Enzyme", J. Pharm. Exp. Therap., Vol. 204, p 271–280 (1978).

The table shows the results obtained after administration of oral doses of the compounds of formula I. The doses were chosen so as to give equimolar amounts of the test compounds in order to eliminate differences due to differences in molecular weight. The inhibition of the angiotensin I pressor response is expressed as the percentage of the response to angiotensin I obtained before the test compound was administered, and was measured at regular intervals during a three-hour period following the administration of the test compound. The maximum percentage inhibition observed during this period is given in the table as a number from 0 to 100 percent. All results are the mean values obtained for testing of each compound in at least four rats. For compounds tested at more than one dose, it can be observed that increased amounts of compound administered lead to increased levels of inhibition.

| | Maximum Percent Inhibition | | | |
|---|---|---|---|---|
| Test Compound | 0.5 | 1.5 | 5 | 15 |
| Example 1 | | 50.30 | 64.50 | |
| Example 2 | | 32.30 | 66.70 | |
| Example 3 | 20.90 | 74.00 | 91.00 | 97.10 |
| Example 4 | 46.60 | 69.00 | 89.90 | |
| Example 5 | 22.20 | 69.00 | 80.50 | |
| Example 6 | | | 64.70 | |
| Example 7 | | | 57.20 | |
| Example 8 | 19.70 | 72.40 | 82.70 | 85.50 |
| Example 9 | 17.90 | 66.50 | 82.10 | 90.30 |
| Example 10 | 45.00 | 66.00 | 75.00 | |
| Example 12 | 16.80 | 51.10 | 82.60 | 93.60 |

What is claimed is:

1. A compound of the formula

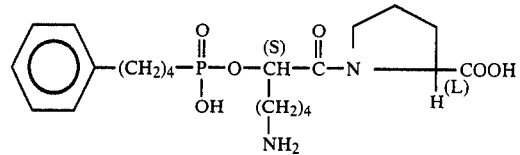

or a pharmaceutically acceptable salt thereof.

2. The compound of claim 1, (S)-1-[6-amino-2-[[hydroxy(4-phenylbutyl)phosphinyl]oxy]-1-oxohexyl]-L-proline, dilithium salt.

3. The compound of claim 1, (S)-1-[6-amino-2-[[hydroxy(4-phenylbutyl)phosphinyl]oxy]-1-oxohexyl]-L-proline.

* * * * *